United States Patent
Fantuzzi et al.

(10) Patent No.: US 10,913,539 B2
(45) Date of Patent: Feb. 9, 2021

(54) FRAGRANCE DELIVERY SYSTEM

(71) Applicant: C&D ZODIAC, INC., Huntington Beach, CA (US)

(72) Inventors: Emmanuel Fantuzzi, Champs sur Marne (FR); Ricardo Padilla, Jr., Orange, CA (US); Romain Ducos, Huntington Beach, CA (US); Ritu Raj Kamal, Ladera Ranch, CA (US); Salar Atabaki, Irvine, CA (US)

(73) Assignee: SAFRAN CABIN INC., Huntington Beach, CA (US)

( * ) Notice: Subject to any disclaimer, the term of this patent is extended or adjusted under 35 U.S.C. 154(b) by 0 days.

(21) Appl. No.: 16/407,834

(22) Filed: May 9, 2019

(65) Prior Publication Data

US 2019/0263527 A1 Aug. 29, 2019

Related U.S. Application Data

(63) Continuation of application No. 15/603,229, filed on May 23, 2017, now Pat. No. 10,287,021, which is a continuation-in-part of application No. 14/942,734, filed on Nov. 16, 2015, now Pat. No. 9,808,550.

(60) Provisional application No. 62/132,433, filed on Mar. 12, 2015, provisional application No. 62/132,431, filed on Mar. 12, 2015, provisional application No. 62/340,378, filed on May 23, 2016, provisional application No. 62/414,504, filed on Oct. 28, 2016.

(51) Int. Cl.
| | |
|---|---|
| *B01F 3/04* | (2006.01) |
| *B01F 5/00* | (2006.01) |
| *B64D 13/06* | (2006.01) |
| *B64D 11/00* | (2006.01) |
| *A61L 9/12* | (2006.01) |

(52) U.S. Cl.
CPC ............ *B64D 13/06* (2013.01); *A61L 9/12* (2013.01); *A61L 9/122* (2013.01); *B01F 3/04021* (2013.01); *B01F 3/04085* (2013.01); *B01F 5/00* (2013.01); *B64D 11/00* (2013.01); *A61L 2209/133* (2013.01); *B64D 2013/0603* (2013.01)

(58) Field of Classification Search
CPC .......... B01F 3/04; B01F 3/04021; B01F 5/00; A24F 25/00
USPC ............................................. 261/30, DIG. 88
See application file for complete search history.

(56) References Cited

U.S. PATENT DOCUMENTS

| | | |
|---|---|---|
| 3,259,050 A | 7/1966 | Grimm, III |
| 5,429,180 A | 7/1995 | Nishino |

(Continued)

OTHER PUBLICATIONS

International Search Report and Written Opinion issued in PCT/US17/34062.

*Primary Examiner* — Robert A Hopkins
(74) *Attorney, Agent, or Firm* — Jeffer Mangels; Butler & Mitchell LLP; Brennan C. Swain, Esq.

(57) ABSTRACT

A fragrance dispensing system for an aircraft that includes a fuselage defining a cabin interior and an environmental control system (ECS). The ECS includes a source of air that moves air between the source of air and the cabin interior along an airflow path, a mixer unit in airflow communication with the source of air and positioned downstream from the source of air in the airflow path, at least a first air duct positioned in the airflow path between the mixer unit and the cabin interior, and a fragrance dispensing unit positioned between the air source and the cabin interior along the airflow path. The fragrance dispensing unit is configured to dispense at least a first fragrance into the airflow path.

13 Claims, 32 Drawing Sheets

(56) References Cited

U.S. PATENT DOCUMENTS

| | | | |
|---|---|---|---|
| 5,924,597 | A | 7/1999 | Lynn |
| 6,371,451 | B1 | 4/2002 | Choi |
| 9,957,052 | B2 | 5/2018 | Fox |
| 2005/0220664 | A1 | 10/2005 | Hitzler |
| 2007/0041865 | A1 | 2/2007 | Ayoub |
| 2008/0093474 | A1 | 4/2008 | Suissa |
| 2009/0311138 | A1 | 12/2009 | Klaptchuk |
| 2011/0290903 | A1 | 12/2011 | Nagano |
| 2016/0101669 | A1 | 4/2016 | Park et al. |

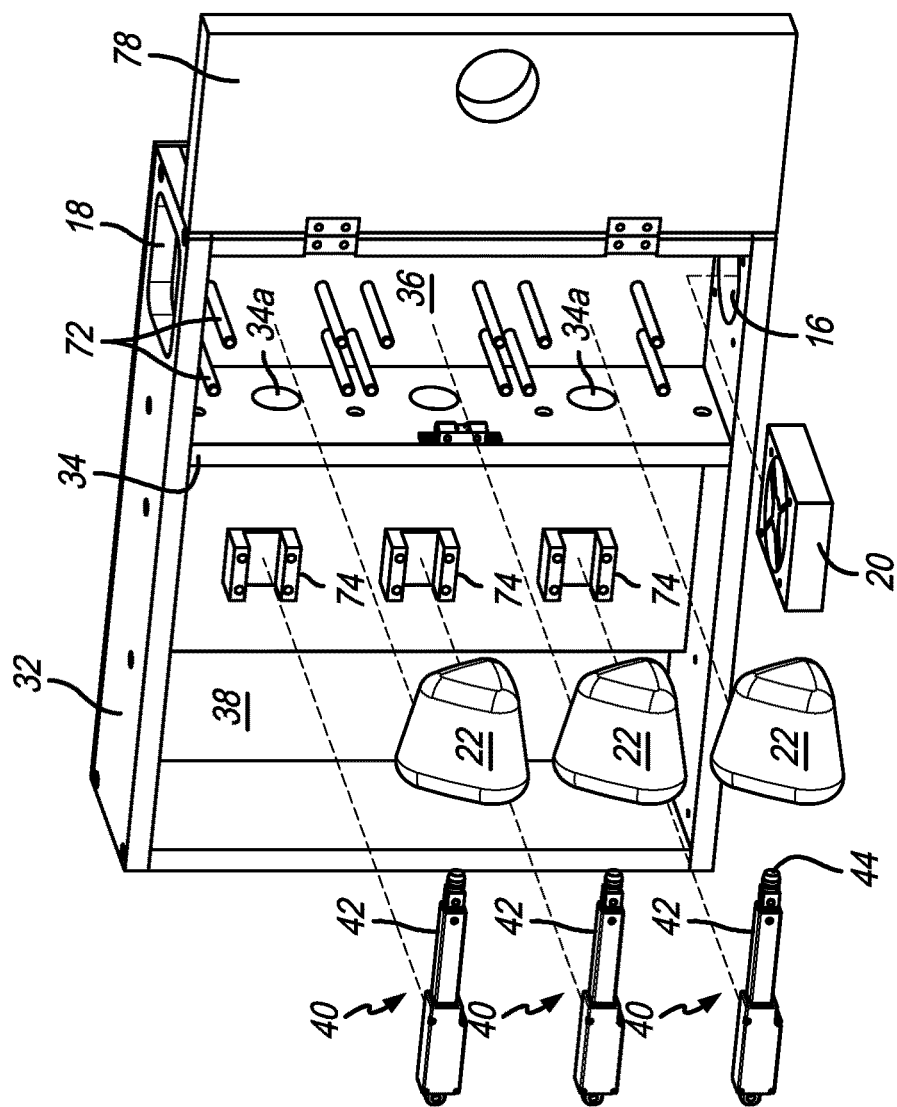
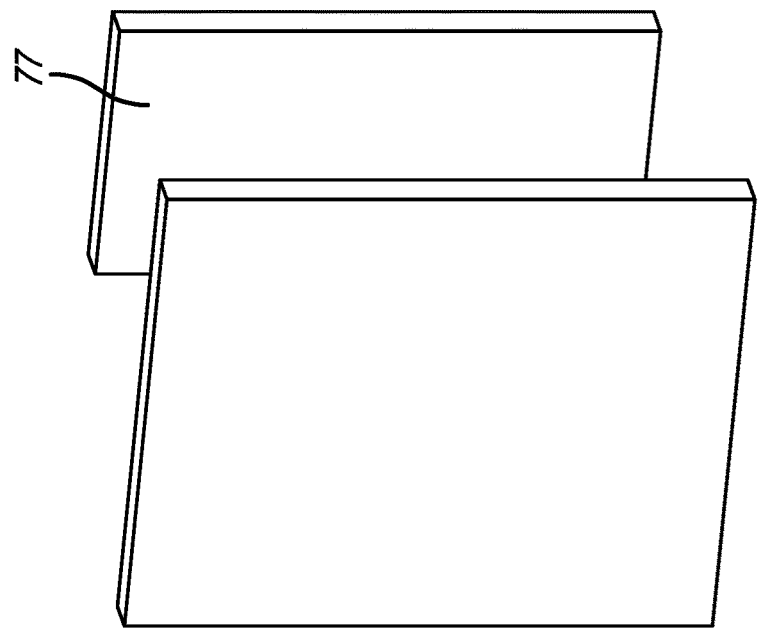
FIG. 5

FRAGRANCE DELIVERY SYSTEM

CROSS REFERENCE TO RELATED APPLICATIONS

This application is a continuation of U.S. patent application Ser. No. 15/603,229 filed May 23, 2017, which is a continuation-in-part of U.S. patent application Ser. No. 14/942,734, filed Nov. 16, 2015, which claims the benefit of U.S. Provisional Application No. 62/132,433, filed Mar. 12, 2015, and U.S. Provisional Application No. 62/132,431, filed Mar. 12, 2015. U.S. patent application Ser. No. 15/603,229 also claims the benefit of U.S. Provisional Application No. 62/340,378, filed May 23, 2016 and U.S. Provisional Application No. 62/414,504, filed Oct. 28, 2016. All of the above listed applications are incorporated by reference herein in their entireties.

FIELD OF THE INVENTION

The present invention relates generally to a fragrance delivery system, and more particularly for a fragrance delivery system for use in an aircraft.

BACKGROUND OF THE INVENTION

Aircraft often include confined spaces. A passenger's experience within those confined spaces can be improved through better scents. High end scent generation is today available in multiple forms. For example, scent marketing is used to enhance customer experience in retail stores, food and beverage stores, casino and hotels. The aim is typically to put the customer in a positive mood or to otherwise make the customer feel comfortable.

SUMMARY OF THE PREFERRED EMBODIMENTS

In accordance with a first aspect of the present invention there is provided a fragrance dispensing system for an aircraft that includes a fuselage defining a cabin interior and an environmental control system (ECS). The ECS includes a source of air that moves air between the source of air and the cabin interior along an airflow path, a mixer unit in airflow communication with the source of air and positioned downstream from the source of air in the airflow path, at least a first air duct positioned in the airflow path between the mixer unit and the cabin interior, and a fragrance dispensing unit positioned between the air source and the cabin interior along the airflow path. The fragrance dispensing unit is configured to dispense at least a first fragrance into the airflow path.

In a preferred embodiment, the first fragrance dispensing unit includes a scent assembly that contains a first fragrance oil that comprises the first fragrance. Preferably, the first fragrance dispensing unit is configured to selectively dispense at least first and second fragrances into the airflow path. In a preferred embodiment, the first fragrance dispensing unit is configured to dispense the first fragrance into the mixer unit or at another point between the air source and a point where the airflow path splits off into separate ducts. In a preferred embodiment, the first fragrance dispensing unit includes a first fragrance cartridge therein that includes a scent assembly with the first fragrance therein. The first fragrance cartridge includes a cover that is movable between a closed position and an open position and the first fragrance is dispensed when the cover is in the open position. In an embodiment, the first fragrance dispensing unit also includes a second fragrance cartridge therein that includes a scent assembly with a second fragrance. The second fragrance cartridge includes a cover that is movable between a closed position and an open position where the second fragrance is dispensed.

In a preferred embodiment, at least first and second air ducts are positioned in the airflow path between the mixer unit and the cabin interior and the cabin interior includes at least first and second zones. The first fragrance dispensing unit is positioned between the mixer unit and the cabin interior and is configured to dispense the first fragrance into the first duct along the airflow path and into the first zone and a second fragrance dispensing unit is positioned between the mixer unit and the cabin interior and is configured to dispense the first fragrance (which may be the same scent or a different scent as what is dispensed from the first fragrance dispensing unit) into the second duct along the airflow path and into the second zone. Preferably, the first and second fragrance dispensing units are separately controllable so that fragrances can be delivered to the first and second zones as desired. In another embodiment the first and second fragrance dispensing units can be controlled together.

In a preferred embodiment, the first fragrance dispensing unit is configured to selectively dispense at least first and second fragrances into the first duct and the second fragrance dispensing unit is configured to selectively dispense at least first and second fragrances into the second duct. Preferably, the first fragrance dispensing unit includes a first fragrance cartridge therein that includes a scent assembly with the first fragrance therein. The first fragrance cartridge includes a cover that is movable between a closed position and an open position, such that the first fragrance is dispensed when the cover is in the open position. Preferably, the first fragrance dispensing unit includes a second fragrance cartridge therein that includes a scent assembly with the second fragrance therein. The second fragrance cartridge includes a cover that is movable between a closed position and an open position, such that the second fragrance is dispensed when the cover is in the open position.

In a preferred embodiment, the fragrance dispensing unit is in electrical communication with an electrical control unit and the first fragrance dispensing unit is configured to selectively dispense the first fragrance based on instructions from the electrical control unit. Preferably, the electrical control unit includes a human machine interface, and the instructions can be provided via human input. The human machine interface can be associated with or on the electrical control unit or can be a separate unit, such as a portable touch screen display.

In accordance with another aspect of the present invention there is provided an aircraft that includes a fuselage defining a cabin interior, and a fragrance delivery system disposed in the cabin interior. The fragrance delivery system includes a first fragrance dispensing unit that includes a first fragrance cartridge with a first scent and a second fragrance cartridge with a second scent, a first electronic control unit in communication with the first fragrance dispensing unit, and a human machine interface in communication with the first electronic control unit. The first fragrance dispensing unit is configured to selectively dispense either the first fragrance or the second fragrance.

In a preferred embodiment, the cabin interior is divided into at least first and second zones. The first fragrance dispensing unit is positioned in the first zone and a second fragrance dispensing unit is positioned in the second zone. The second fragrance dispensing unit is in communication with a second electrical control unit and the second electrical control unit is in communication with the human machine interface. In a preferred embodiment, a third fragrance dispensing unit is positioned in the first zone. The third fragrance dispensing unit is in communication with the first electrical control unit. The first and third fragrance dispensing units can be controlled together (such that they dispense the same fragrance) or separately.

In a preferred embodiment, the first fragrance dispensing unit includes a first fragrance cartridge therein that includes a first near field communication portion that includes information related to the first fragrance cartridge stored therein. The first near field communication portion is in communication with a receiver in the first fragrance dispensing unit, which in turn transmits the information related to the first fragrance cartridge to the electrical control unit and ultimately to the human machine interface (where it can be displayed).

In accordance with yet another aspect of the present invention there is provided a fragrance dispensing unit that includes a housing that defines an interior and includes at least one intake opening and at least one outlet opening and an airflow path that is defined between the intake opening and the outlet opening. The unit also includes a fan positioned along the airflow path, and at least a first cartridge positioned along the airflow path. The first cartridge includes a cover that is movable between a closed position and an open position, and includes a scent assembly that is not in flow communication with the airflow path when the first cover is in the closed position and that is in flow communication with the airflow path when the first cover is in the open position.

In a preferred embodiment, the first cartridge is removably received in a first fragrance module and includes a near field communication transmitter therein that includes information about the first cartridge stored therein. The first fragrance module includes a near field communication receiver for receiving the information about the first cartridge. Preferably, the fragrance delivery unit also includes a second cartridge positioned along the airflow path that is removably received in a second fragrance module. The second cartridge includes a cover that is movable between a closed position and an open position and includes a near field communication transmitter therein that includes information about the second cartridge. The second fragrance module includes a near field communication receiver for receiving the information about the first cartridge.

In a preferred embodiment, the first fragrance module includes a rotatable portion that is in engagement with the first cartridge. Rotational movement of the rotatable portion moves the cover of the first cartridge between the open and closed positions along a linear path.

In accordance with another aspect of the present invention there is provided a method of dispensing fragrances in an aircraft that includes an environmental control system. The method includes positioning a fragrance dispensing unit at a point along an airflow path between an air source (e.g., an engine or APU) and the cabin interior. The method can also include dispensing a first fragrance from the fragrance dispensing unit into the airflow path and into the cabin interior, stopping dispensing the first fragrance and then dispensing a second fragrance from the fragrance dispensing unit into the airflow path and into the cabin interior. The fragrance dispensing unit can be positioned to dispense the first and/or second fragrances at a point between the air source and the mixer unit, into the mixer unit and/or between the mixer unit and the cabin interior. The method can also include providing or obtaining a plurality of fragrance dispensing units and positioning them between the mixer unit and the cabin interior such that they each can dispense a fragrance or fragrances into separate ducts each associated with a different zone in the aircraft.

In accordance with another aspect of the present invention there is provided a scent delivery assembly that includes a main body portion that defines an interior and includes at least one intake opening and at least one outlet opening, an airflow path that is defined between the intake opening and the outlet opening, a fan positioned along the airflow path, and at least a first cartridge positioned along the airflow path. The first cartridge includes a first cover that is movable between a closed position and an open position and a scent assembly. The scent assembly is not in flow communication with the airflow path when the first cover is in the closed position, and the scent assembly is in flow communication with the airflow path when the first cover is in the open position. In a preferred embodiment, the scent assembly includes a reservoir portion and a diffusing portion. Preferably, the scent delivery system also includes a second and third cartridges positioned along the airflow path. In a preferred embodiment, each of the cartridges has a different scent associated therewith. Preferably, the scents are chosen to affect a user or passenger's mood. For example, the scents can be chosen to energize, calm, relax, etc. Preferably, the scent delivery assembly also includes a controller that is configured to selectively move the first, second and third covers between the open and closed positions.

In a preferred embodiment the scent delivery assembly includes a first actuator that includes a first arm that is movable between a first position and a second position. The first cartridge is attached to a distal end of the first arm. When the first arm is in the first position the first cover is in the closed position and when the first arm is in the second position the first cover is in the open position. Preferably, the main body portion includes a divider member positioned in the interior that divides the interior into an airflow path portion and a non-airflow path portion. The first cartridge is position in the airflow path portion and the first actuator is position in the non-airflow path portion.

In a preferred embodiment, the first cartridge includes a housing portion and the cover portion. The housing portion includes an attachment opening therein and the distal end of the first actuator arm is releasably received in the attachment opening. Preferably, when the first cover is in the closed position the scent assembly is not aligned with the airflow path and when the first cover is in the open position the scent assembly is generally aligned with the airflow path. In a preferred embodiment, the scent delivery system includes at least first and second positioning pegs positioned adjacent an exterior surface of the first cartridge.

In a preferred embodiment, the scent delivery system includes a motor that is operable to move the first cover between the open and closed positions. In a preferred embodiment, the first cartridge includes a second cover that is movable via the motor together with the first cover between the closed position and the open position and the scent assembly is positioned in the airflow path between the first cover and the second cover. In a preferred embodiment, the main body portion includes a lower housing portion and an upper housing portion that cooperate to define the interior and the intake opening is defined in the lower housing portion and the outlet opening is defined in the upper housing portion. Preferably, the scent delivery system includes a removable tray portion received in a tray portion recess defined in the lower housing portion. The tray portion includes a first cartridge opening defined therethrough and the first cartridge is removably received in the first cartridge opening. Preferably, the upper housing portion is pivotally connected to the lower housing portion. In a preferred embodiment, the motor includes an arm extending therefrom that is configured to move the first cover between the open and closed positions. Preferably, the cartridge is sealed when it is in the closed position.

In a preferred embodiment, the first, second and third cartridges each include a scent associated therewith and are configured to communicate the scent to the controller. Preferably, the controller is configured to communicate the scent identification to a control panel (e.g., a tablet, smart phone, etc.) that includes a user interface (such as a graphical user interface on the tablet).

The present invention provides the ability to enrich the air within the cabin of an aircraft with a predetermined scent. In other words, the present invention provides the ability to deliver a scent from a fragrance or the like to a passenger onboard an aircraft.

In a preferred embodiment, the invention includes scent cartridges and a control panel (such as a tablet or other remote control) for controlling the delivery of the scented air.

When used, the present invention can enhancing passengers' mood on an aircraft. In a preferred embodiment, the system includes the ability to control at least one of the scent of the cabin, the lighting (mood lighting), the music, the inflight entertainment and the cabin temperature. The ability to control one or all of these items helps set the mood of the cabin and can bring added value to the passenger experience. Being able to control remotely or not the scent/fragrance diffused in the cabin or part of the cabin (e.g., a private room) of an aircraft together with ambient/personal lights and/or sound (music) and/or entertainment system and/or environmental control system provide the ability to diffuse and control the scent in the cabin/part of cabin. Combined control of ambiance featured by the different scent diffused in the cabin and/or the light and/or sound effect to set a specific mood.

The control panel/tablet can be in communication with the controller within the scent delivery system via a wired or wireless (e.g., Wi-Fi) connection. Preferably, the scent delivery system includes a plurality of cartridges that can provide different scents as desired by the user. The controller also preferably controls the fan settings (e.g., speed, duration, number of cycles, etc.). For example, the fan may run one minute on and then two minutes off or two minutes at a reduced speed. The controller also preferably controls the opening and closing of the cartridges to enhance the scent experience by passengers.

As described herein and shown in the accompanying drawings, the present invention provides the ability for in-flight fragrance delivery onboard an aircraft. In-flight fragrance delivery includes exemplary embodiments disclosed herein and in the accompanying drawings that include in-flight fragrance delivery in VVIP and VIP aircraft, business aviation aircraft and commercial aviation aircraft. Additional embodiments can similarly include military aircraft, medical aircraft and experimental aircraft.

VVIP and VIP Aircraft include the ultimate top-of-the-line aircraft accommodation experience with the most luxurious accoutrements. This embodiment includes fragrance delivery for each "room" or zone within the aircraft, independent of or integrated with the Environmental Control System (ECS) zones. In use, a user selects independent fragrances from a palette or controller for each zone, multiple zones or the entire cabin. The fragrance can be turned on and off for each zone independently, multiple zones or the entire cabin. Fragrances can be selected from a library of catalog fragrances, a duplicated fragrance experience or custom designed fragrances. The fragrance delivery system can be integrated into the aircraft ECS or be a stand-alone supplement to the ECS. Fragrance control can be integrated into the aircraft Cabin Management System (CMS) or a stand-alone supplement to the CMS.

Business aviation aircraft include an upscale experience on aircraft dedicated for business or personal use. These aircraft are often outfitted with upscale accommodations for passengers. This embodiment includes consistent fragrance delivery for the entirety of the aircraft passenger space, independent of or integrated with the Environmental Control System (ECS) zones or for individual zones. Fragrances can be selected from a library of catalog fragrances, a duplicated fragrance experience or custom designed fragrances. The fragrance delivery system can be integrated into the aircraft ECS or be a stand-alone supplement to the ECS. Fragrance control can be integrated into aircraft Cabin Management System (CMS) or a be a stand-alone supplement to the CMS.

Commercial aviation aircraft are often outfitted with varying levels of accommodations for passengers. The fragrance delivery can be employed for the entirety of the aircraft passenger space, seating class zones or individualized for each passenger space. The fragrance delivery operates independent of or can be integrated with the Environmental Control System (ECS) zones. Fragrances can be selected from a library of catalog fragrances, a duplicated fragrance experience or custom designed fragrances. Fragrance control can be integrated into aircraft Passenger Service Unit (PSU) controls, the In Flight Entertainment (IFE) system or a be a stand-alone control system.

The fragrance dispersion unit taught herein contains single or multiple fragrance cartridge modules. Each module houses one fragrance that can be presented to be used upon demand. The fragrance cartridge is self-sealing and houses a wetted fragrance wick. The drive motor in the fragrance module opens the cartridge on demand and exposes the wetted wick to a forced airflow provided by an electric fan within the fragrance dispersion unit (FDU). The fragrance cartridge also contains a near field communication (NFC) chip which is encoded with information, such as, the name of the fragrance, the manufacturing date, a unique identifier, and a color code. The NFC chip communicates the encoded information to the controller or controllers (see, e.g., FIGS. 26-29). The fragrance name and color code are used to display information for the user on the controller or controllers. The manufacturing date is used to monitor shelf life and cartridge usage life to the controller. Usage life is limited to ensure the quality of the fragrance throughout its life. The data is encrypted to make the cartridge tamper resistant. The controller keeps track of which fragrance cartridges are installed in each FDU or each zone if multiple FDU's are installed in a common zone.

Preferably, the fragrance module contains a drive motor to open the cartridge and an NFC reader to decode the NFC chip once the cartridge is inserted into the fragrance module. Information is transmitted to the controller or controllers which recognize the cartridge as new or in use and then displays it as an available fragrance on the human machine interface (HMI) touch screen. The controller utilizes a user friendly graphical user interface (GUI) on a touch-screen device for human interaction. The controller software maps all the available fragrances in each aircraft zone in its memory which can be accessed through a series of menus on demand. To activate a fragrance, the user selects an aircraft zone and is presented a list of available fragrances for that zone. Upon selection of the desired fragrance, the controller commands the FDU or FDU's in the selected zone to open the fragrance cartridge and operate the fan for fragrance dispersion. In a preferred embodiment, the controller keeps track of the usage time for each cartridge, notifying the user when a cartridge should be replaced. A localized LED light on the FDU or on each individual fragrance module is used to help identify which cartridge is to be replaced.

The controller can be a wired connection or a wireless device and the controller functions can be integrated into a central Cabin Management System (CMS).

The fragrance dispensing system taught herein can be integrated into the typical aircraft ECS. In a typical ECS, compressed air is taken off the engines, the auxiliary power unit (APU) or a ground cart. The air then goes through the A/C packs to cool it through a process of compression and expansion cycles. There are filters and water separators in the A/C packs as well. From there, the air is fed into the mixer unit where it is mixed with recirculated cabin air. For temperature control, the air is then fed through a heat exchanger. An alternate method for temperature controls is to pump uncooled bleed air into the mixer unit as well. From there, the conditioned and temperature controlled air is fed into the cabin. There are different duct lines for different zones in the cabin. Some of the air that is displaced from the cabin is dumped overboard and some is recirculated back into the mixer unit.

In the present invention, fragrance can be delivered into the cabin in two ways using the ECS. The first is inject it into the mixer unit. This yields evenly dispersed fragrance throughout the entire cabin. This scenario may be used by airlines and operators that are, for example, self-promoting their "scent brand" (i.e., passengers will associate the scent of the cabin with the airline). Alternatively, the fragrance can be introduced in the ducts between the mixer unit and the cabin sections. This allows for fragrance scenting cabin areas independently (e.g., different classes can be scented differently). The fragrance dispensing system can be controlled automatically such that fragrances are dispensed at predetermined times or at predetermined altitudes or the fragrance dispensing system can be controlled by a human machine interface, as described above.

It will be appreciated that business jet ECS's work similarly, but some do not recirculate cabin air. Business jets are also limited from one to four cabin zones. See also, U.S. Patent Publication No. 2015/0019029, the entirety of which is incorporated by reference herein.

BRIEF DESCRIPTION OF THE DRAWINGS

The invention may be more readily understood by referring to the accompanying drawings in which:

FIG. 5 is an exploded perspective view of the scent delivery assembly of FIG. 1;

Like numerals refer to like parts throughout the several views of the drawings.

DETAILED DESCRIPTION OF THE PREFERRED EMBODIMENTS

Figure 1:
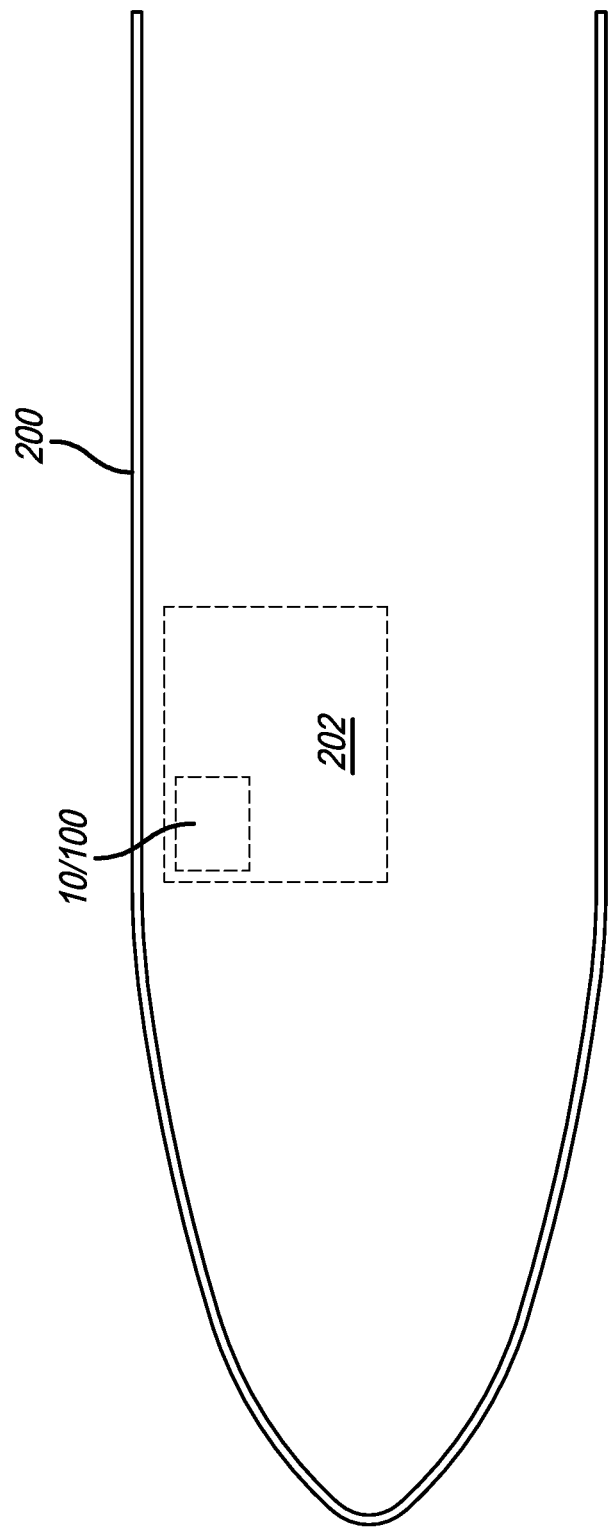
FIG. 1 is a plan view of an aircraft with a private room therein that includes a scent delivery system in accordance with a preferred embodiment of the present invention.
Figure 2:
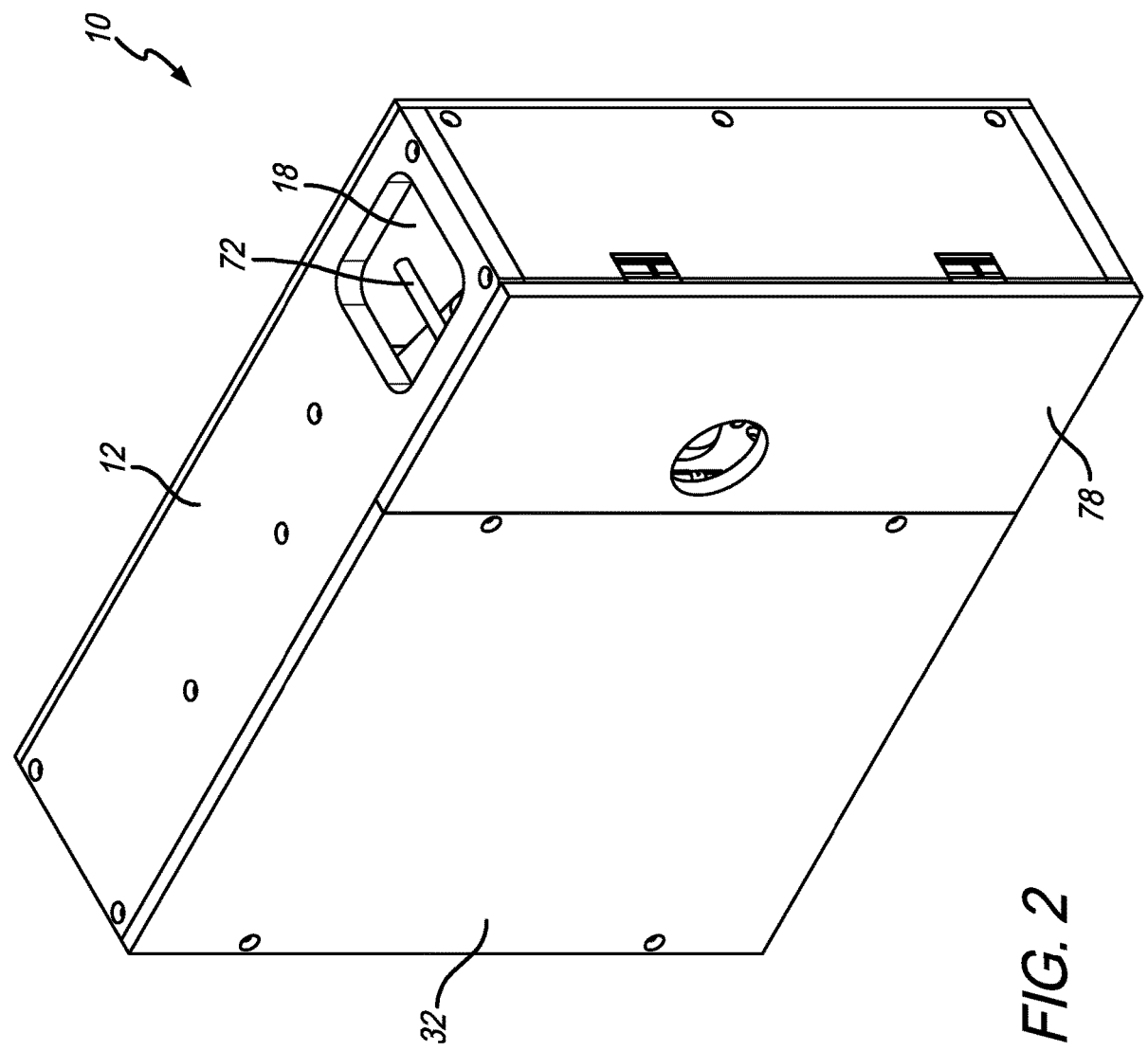
FIG. 2 is a perspective view of a scent delivery assembly in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, wherein the showings are for purposes of illustrating the present invention and not for purposes of limiting the same, FIGS. 1-13 show embodiments of scent delivery systems or assemblies 10 and 100. In a preferred embodiment, the scent delivery assemblies are used in the interior of aircraft, as shown in FIG. 1. However, this is not a limitation on the present invention and the scent delivery assemblies 10 and 100 can be used elsewhere.

Figure 3:
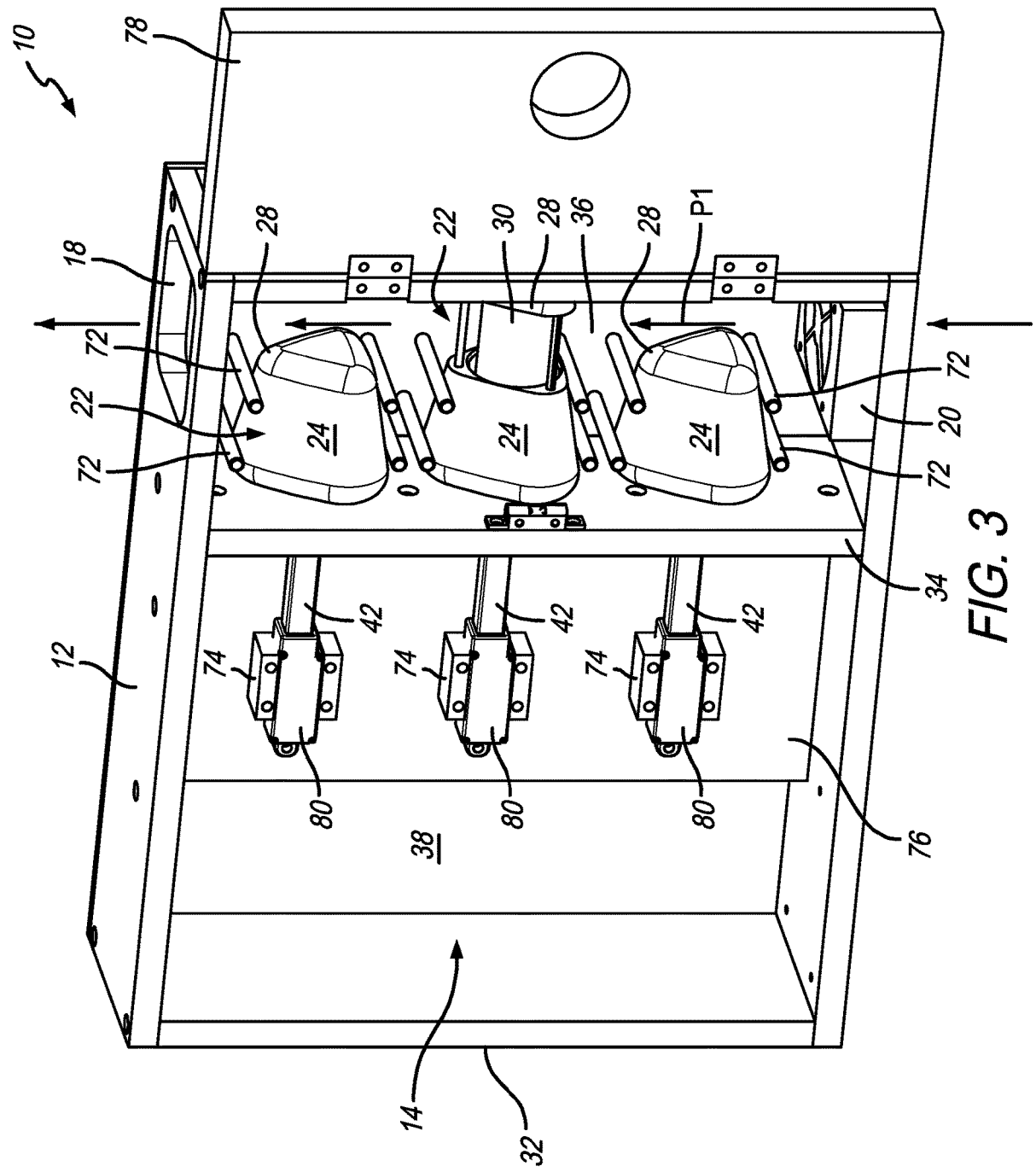
FIG. 3 is a perspective view of the scent delivery assembly of FIG. 1 with a portion of the housing removed.
Figure 4:
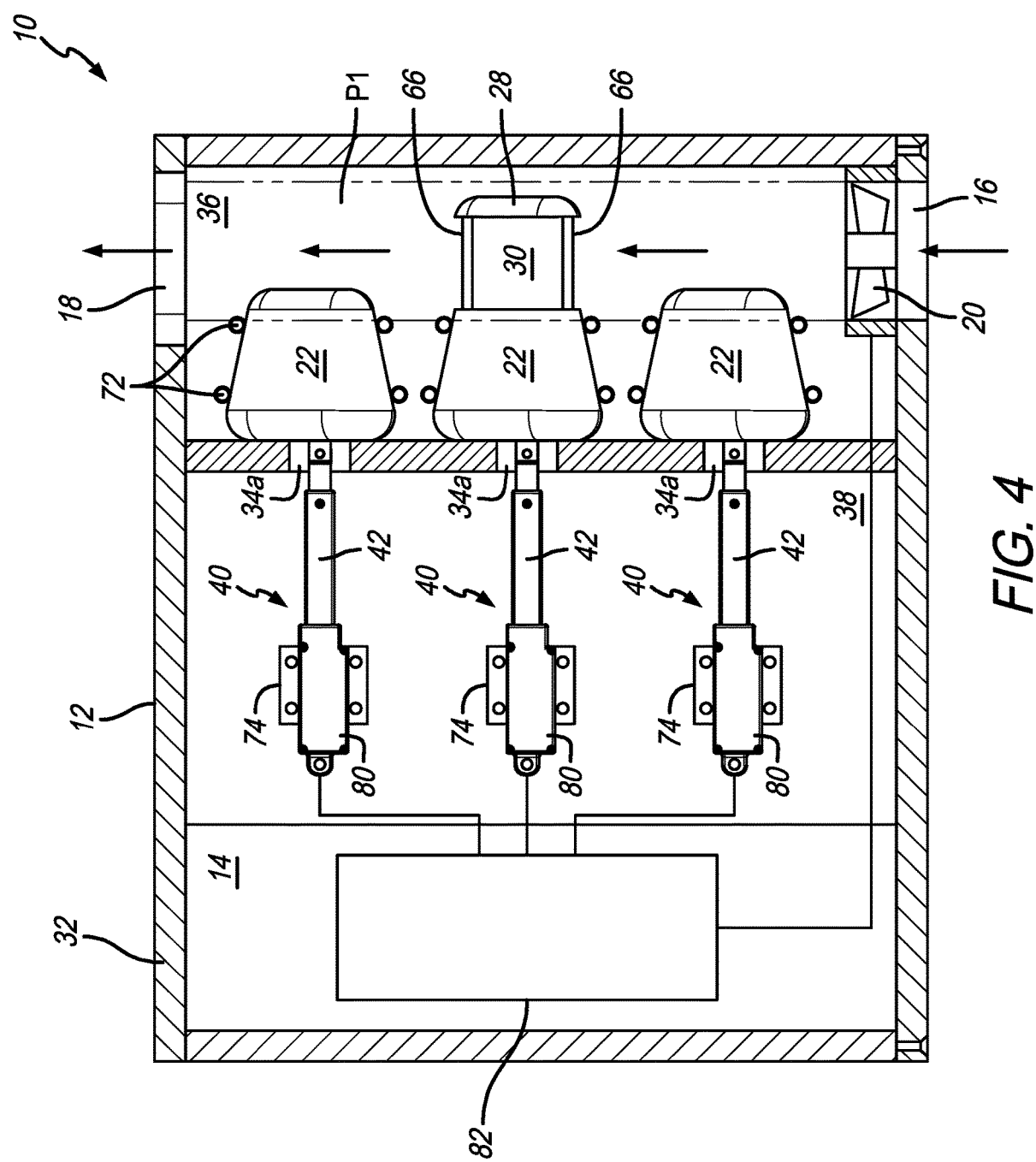
FIG. 4 is a cross-sectional elevational view of the scent delivery assembly of FIG. 1.

With reference to FIGS. 2-8, scent delivery assembly 10 is shown and described. In a preferred embodiment, scent delivery assembly 10 includes a main body portion 12 that defines an interior 14 and includes at least one intake opening 16 and at least one outlet opening 18. As shown in FIGS. 3-4, an airflow path P1 is defined between the intake opening 16 and the outlet opening 18. A fan 20 is positioned along the airflow path P1. At least one and preferably a plurality of cartridges 22 are positioned along the airflow path P1. Each cartridge 22 includes a housing portion 24 that defines a housing interior 26, a cover 28 and a scent assembly 30 positioned in the housing interior 26. The cover 28 is movable between a closed position and an open position. In a preferred embodiment, the scent assembly 30 is movable together with the cover 28 between the closed and opened positions. The scent assembly 30 is not in flow communication with the airflow path P1 when the cover 28 is in the closed position and is in flow communication with the airflow path P1 when the cover 28 is in the open position. FIGS. 3-4 show the middle cartridge 22 with the cover 28 and scent assembly 30 in the open position and the top and bottom cartridges 22 with the cover 28 and scent assembly 30 in the closed position.

As shown in FIGS. 2-5, the main body portion 12 includes a housing 32 having a divider member 34 that divides the interior 14 into an airflow path portion 36 and a non-airflow path portion 38. The cartridges 22 are positioned in the in the airflow path portion 36 and a plurality of actuators 40 are positioned in the non-airflow path portion 38.

Figure 6:
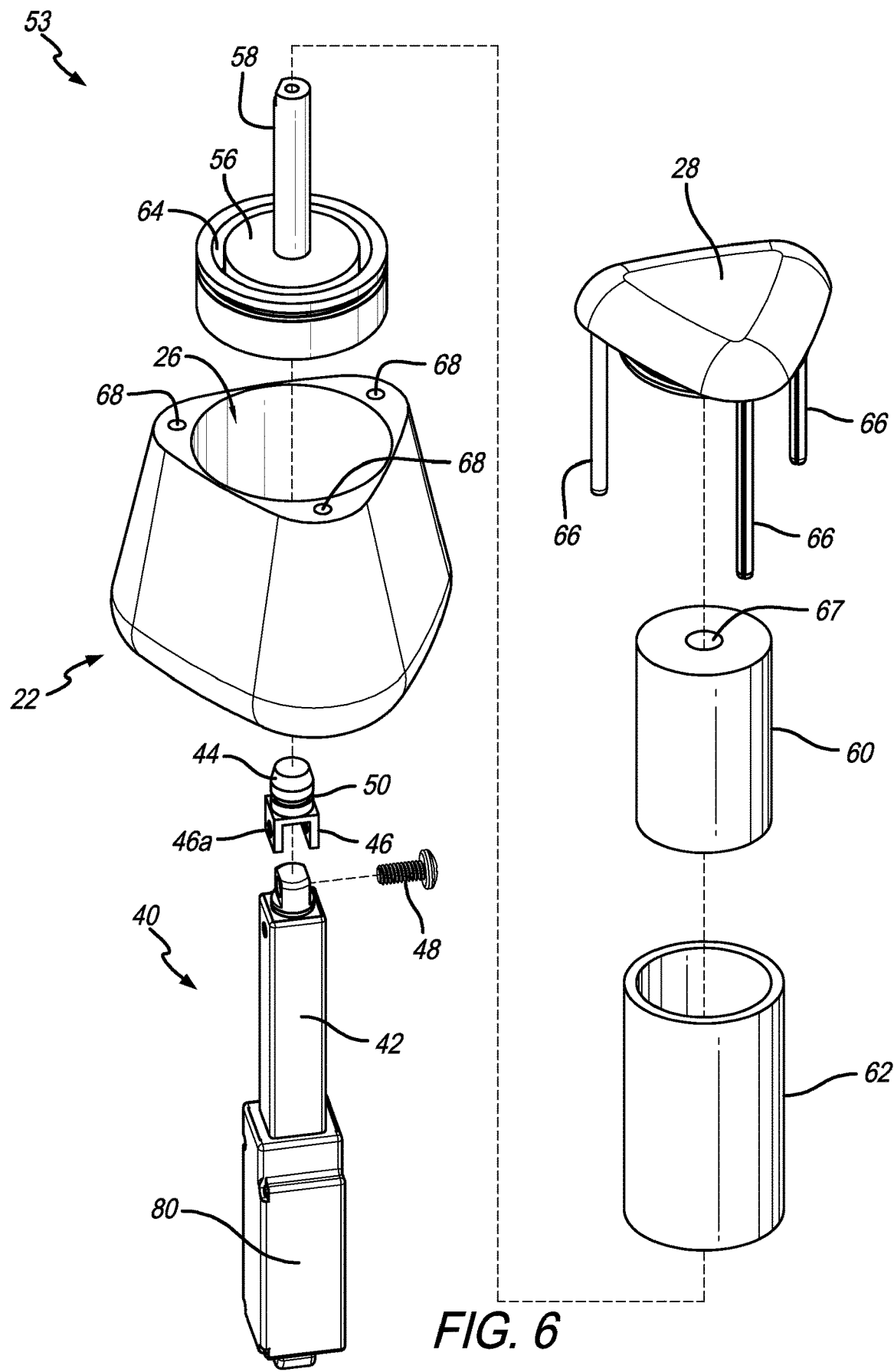
FIG. 6 is an exploded perspective view of a cartridge and actuator from the scent delivery assembly of FIG. 1.
Figure 7:
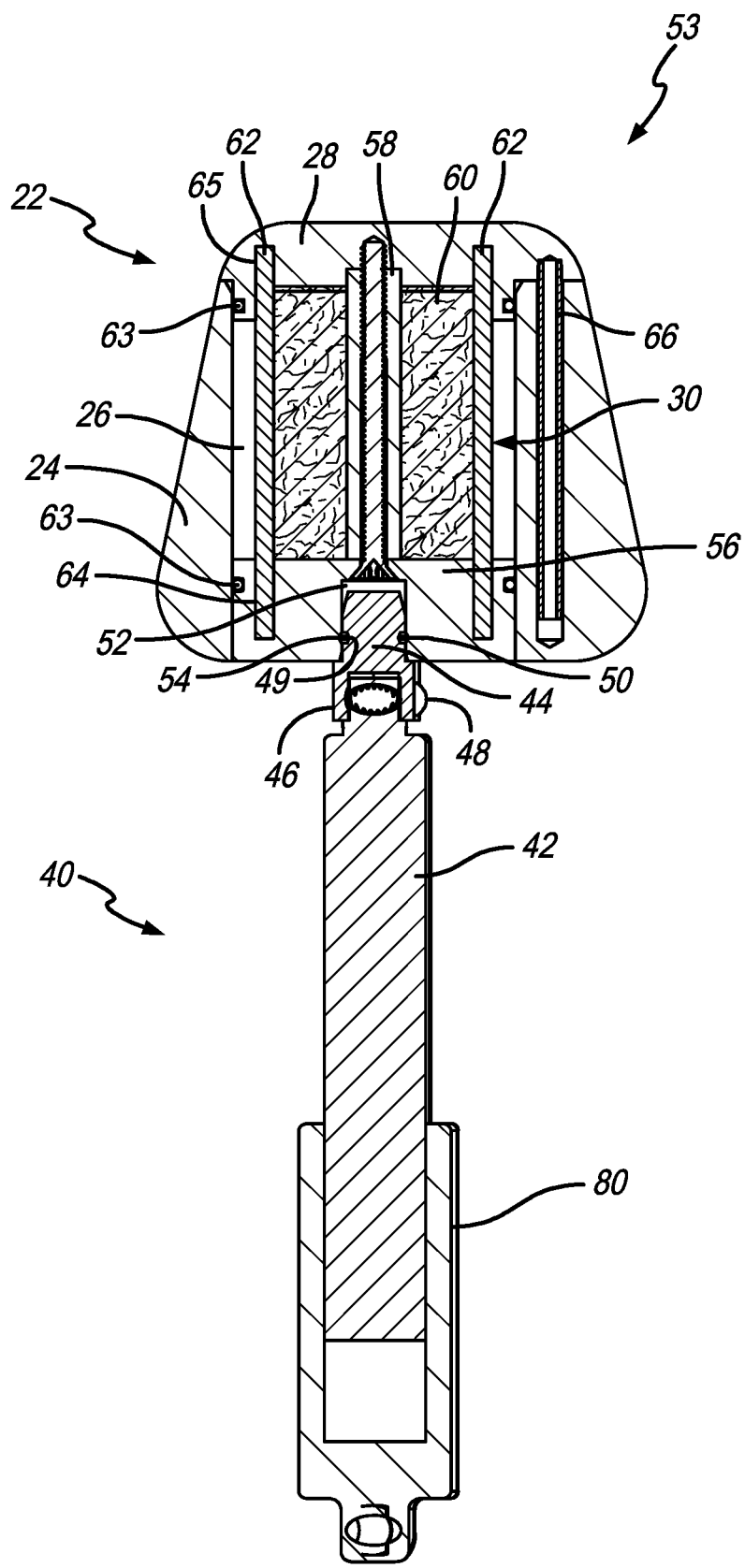
FIG. 7 is a cross-sectional view of a cartridge and actuator from the scent delivery assembly of FIG. 1.

FIGS. 6-7 show a cartridge 22 and actuator 40. In a preferred embodiment, the actuator 40 includes an arm 42 that is movable between a first position and a second position. The cartridge 22 is attached to a distal end of the arm 42. As shown in FIG. 4, the arms 42 extend through openings 34a in the divider member 34. Preferably, the cartridge 22 is removable from the arm 42 so that the cartridges 22 can be replaced during use. The connection between the cartridge 22 and the arm 42 can be any connection that allows the cartridge 22 to be replaced. In a preferred embodiment, the arm 42 includes a connection member 44 on the end thereof. The connection member 44 includes flanges 46 on the bottom thereof that include openings 46a therein that receive a screw 48 to connect the connection member 44 to the arm 42.

As shown in FIG. 7, the connection member 44 also includes a circumferential groove 49 defined in its outer diameter that receives a spring 50 therein. The connection member 44 is received in an opening 52 in the bottom of the cartridge 22. The cartridge 22 includes a groove 54 defined in the inner diameter that receives the spring 50. This provides a snap fit relationship so that the cartridge 22 can be removed from the distal end of the arm 42/connection member 44. It will be appreciated that other methods of connection between the arm and cartridge are within the scope of the present invention, e.g., the cartridge can be threaded onto the arm or a friction fit can be used. The actuator 40 and cartridge 22 are referred to herein together as a cartridge assembly 53. In a preferred embodiment, the force to install and remove the cartridge is sufficiently low to be done by hand (without tools), but enough force is required so that the cartridge is not disconnected during actuator operation and cartridge opening. However, this is not a limitation and in another embodiment, tools can be used.

In a preferred embodiment, the cartridge 22 includes a base member 56 in which opening 52 is defined. The base member 56 includes a shaft 58 extend therefrom that is connected at its distal end to the cover 28. The shaft 58 is the spool that receives the scent assembly 30. In a preferred embodiment, the scent assembly 30 includes a reservoir portion 60 and a diffusing portion 62. The diffusing portion 62 is tubular and is received in a circular groove 64 defined in the base member 56 (a similar circular groove 65 is defined in the cover 28). The reservoir portion 60 is received in the diffusing portion 62 and the shaft 58 is received in a central opening 67 in the reservoir portion 60. In a preferred embodiment, the cartridge includes O-rings 63 that are seated in grooves and that seal the movable cover 28 and base member 56 against the stationary housing portion 24. The O-rings 63 seal the cartridge every time it is closed to prevent scent contamination in the cabin and to prevent mixing of the scents when not in use.

It will be appreciated that the reservoir portion 60 is preferably made of a porous material that is impregnated with scented oil. In the open position, the diffusing portion 62 pulls the oil out of the reservoir portion 60 and evaporates it into the air as a result of the flow of air along the airflow path P1. Preferably, each of the cartridges 22 in the scent delivery assembly 10 includes a different scented oil in the reservoir portion 60. The scents can be diffused to instill different moods or simply different scents into the environment (e.g., the room 202 or volume within the aircraft 200; see FIG. 1). It will be appreciated that the scent assembly 30, including the reservoir portion 60 and the diffusing portion 62 can be any shape and is not limited to the cylindrical shape shown. For example, the scent assembly 30 can include a plurality of fins that extend in the same direction as the airflow. In another embodiment, the scent assembly 30 can include a plurality of openings therein. Generally, the scent assembly 30 includes the reservoir portion 60 that holds the scented oil and the diffusing portion 62. Any shape of the components is within the scope of the present invention provided the airflow flows over or through the diffusing portion and pulls the oil from the reservoir portion and moves the scent out in to the environment.

In a preferred embodiment, the cover 28 includes at least one and preferably three alignment rods 66 that extend therefrom and into alignment openings 68 that are defined in the housing portion 24. The movable portion of the cartridge 22 (e.g., the base member 56, scent assembly 30, cover 28, shaft 58 and alignment rods 66, etc.) are referred to together herein as the movable portion 70.

In a preferred embodiment, the scent delivery system 10 includes a plurality of positioning pegs 72 positioned adjacent the exterior surface of the cartridges. The positioning pegs 72 make it easier to position the cartridge 22 when replacing a used one with a new one and are provided for fixing or clamping the housing portion 24 within the airflow path portion 36.

As shown in FIGS. 3-5, in a preferred embodiment, the actuators 40 are attached via brackets 74 that are mounted on a mounting board 76 positioned in the non-airflow path portion 38. Another board 77 can be mounted on the opposite side of the actuators 40. In a preferred embodiment, the airflow path portion 38 is covered by a door 78 that is openable to replace the cartridges 22.

The actuators 40 can include any type of mechanism capable of extending the arm 42 in a linear manner. In a preferred embodiment the arm 42 is movable within a housing 80 that slidably receives the arm and houses the mechanism for extending and retracting the arm 42. The electronics for the actuator 40 are also preferably housed in the housing 80. The actuators 40 are in communication with and controlled by a controller 82 that is part of a printed circuit board or the like.

Figure 8:
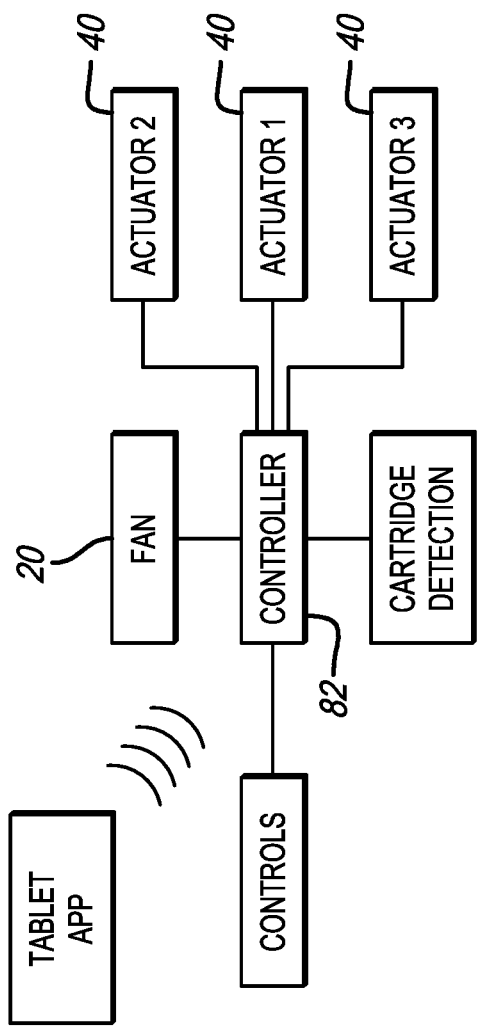
FIG. 8 is a schematic showing the communication between the controller, the cartridges and the fan.

FIG. 8 shows an exemplary embodiment of the communication between the controller 82 (which is preferably part of a PCB), the actuators 40, the fan 20, and the control panel. The controller and PCB are capable of communicating with the control panel (e.g., tablet, smart phone) wirelessly or on a device with buttons. It provides the actuators and fan proper input settings for selecting the proper cartridge (from user selection) and proper settings (fan speed etc.) depending on room size, scent selected, etc.

In a preferred embodiment, the controller 82 is in communication with the cartridges (e.g., through RFID or other wireless communication) so that the controller 82 can identify the particular scent associated with the cartridge and to monitor the cartridge (e.g., scent oil remaining, how long the cartridge has been in use, etc.). For example, the cartridge can include an RFID tag or other transmitter attached thereto and the controller can include a receiver to recognize the cartridge scent once installed. This will then populate the control pad or other human machine interface (e.g., tablet) so that it is apparent what scent is in the particular cartridge (e.g., energetic, calming, relaxing, etc.). Generally, it will be appreciated that the controller 82 can selectively move the covers 28 (and, therefore, the scent assemblies 30) between the open and closed positions.

In use, when a user wants to diffuse a scent into the environment, the user pushes a button or the like on the tablet or other control panel. The tablet communicates with the controller 82 of the scent delivery assembly 10, which, in turn, actuates the actuator 40 of the appropriate cartridge assembly 53. When the actuator 40 is actuated arm 42 moves from the first position to the second position and the movable portion 70 (which includes the cover 28) is moved from the closed position to the open position. Because the distal end of arm 42 is engaged with opening 52, as arm 42 moves to the second position it moves base member 56, which moves the scent assembly 30 and shaft 58 together with cover 28. The alignment rods 66 also move within alignment openings 68. The controller 82 also actuates fan 20, thereby pulling air through intake opening 16 and moving air along airflow path P1. As a result of air flowing over the exposed diffusing portion 62, oil is pulled from the reservoir portion 60, is expelled through outlet opening 18 and released into the environment.

In a preferred embodiment, as shown in FIG. 4, the cartridges 22 are positioned so that the scent assemblies 30 are generally out of the air flow path P1 when the covers 28 are in the closed position, and are extended into or are aligned with the airflow path P1 when the covers 28 are in the open position.

Figure 9:
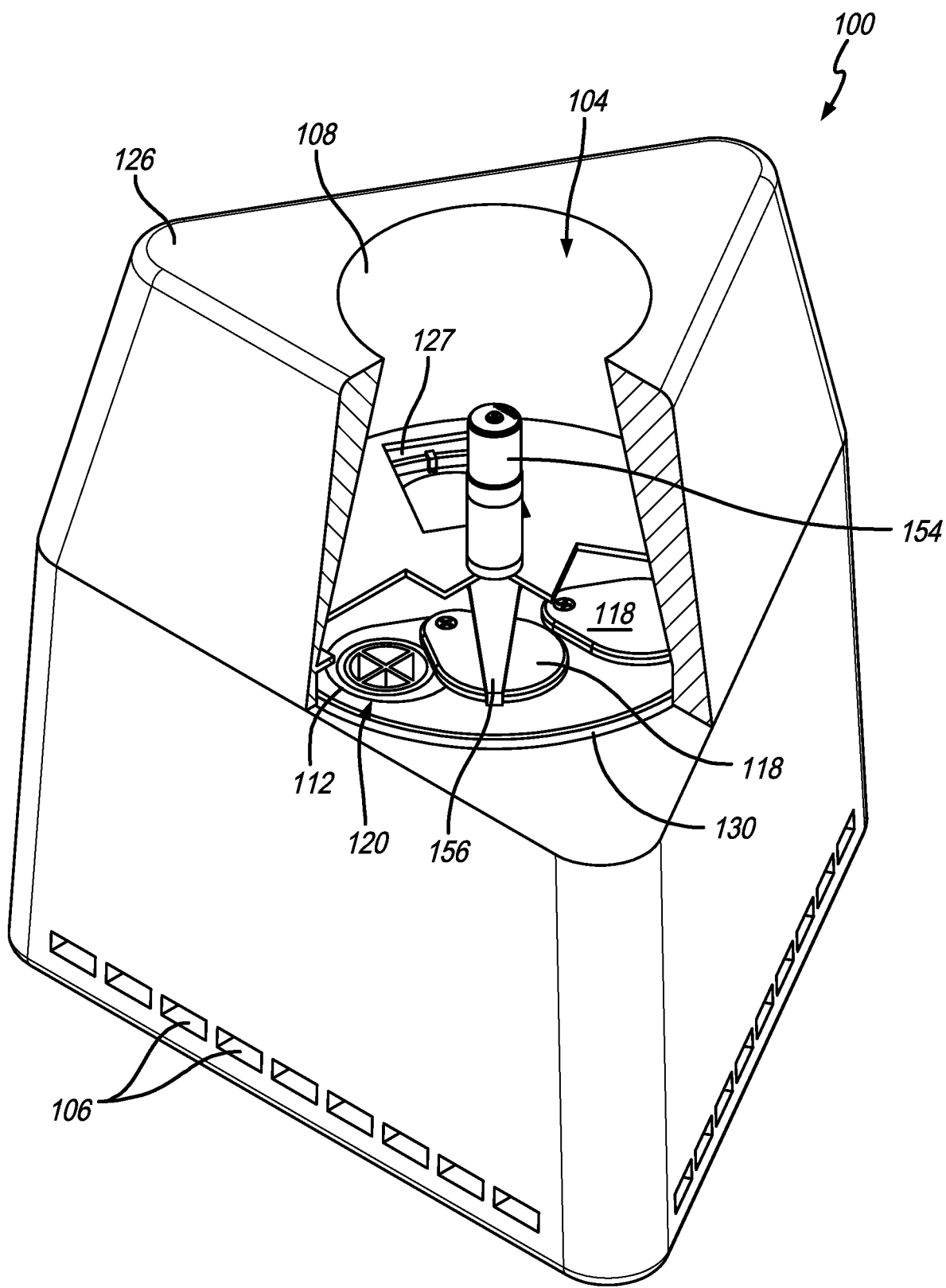
FIG. 9 is a perspective view of a scent delivery assembly in accordance with a preferred embodiment of the present invention with a portion of the upper housing portion cut away.
Figure 10:
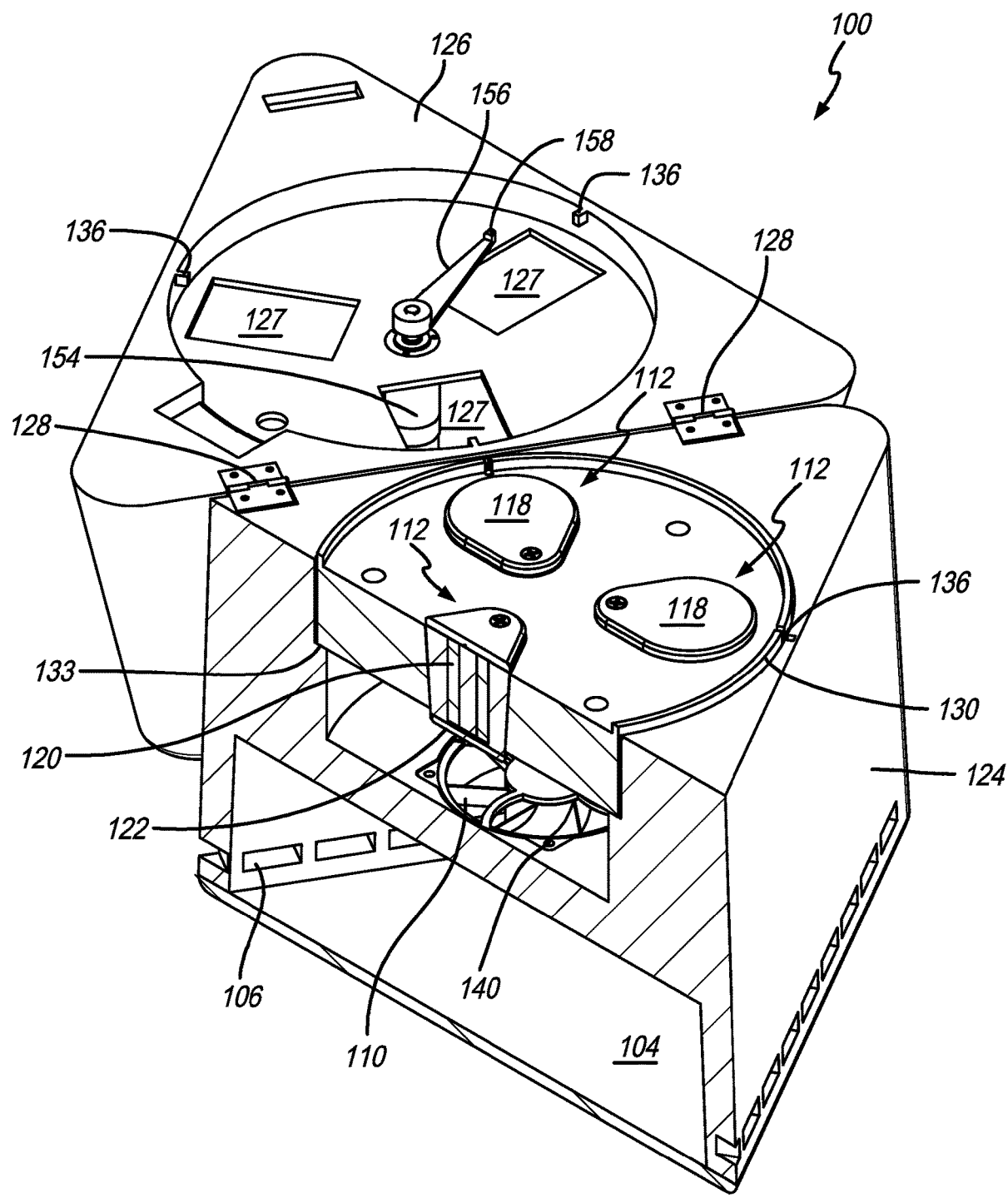
FIG. 10 is a perspective view of the scent delivery assembly of FIG. 9 with the upper housing portion hinged open and a portion of the lower housing portion in cross-section.
Figure 11:
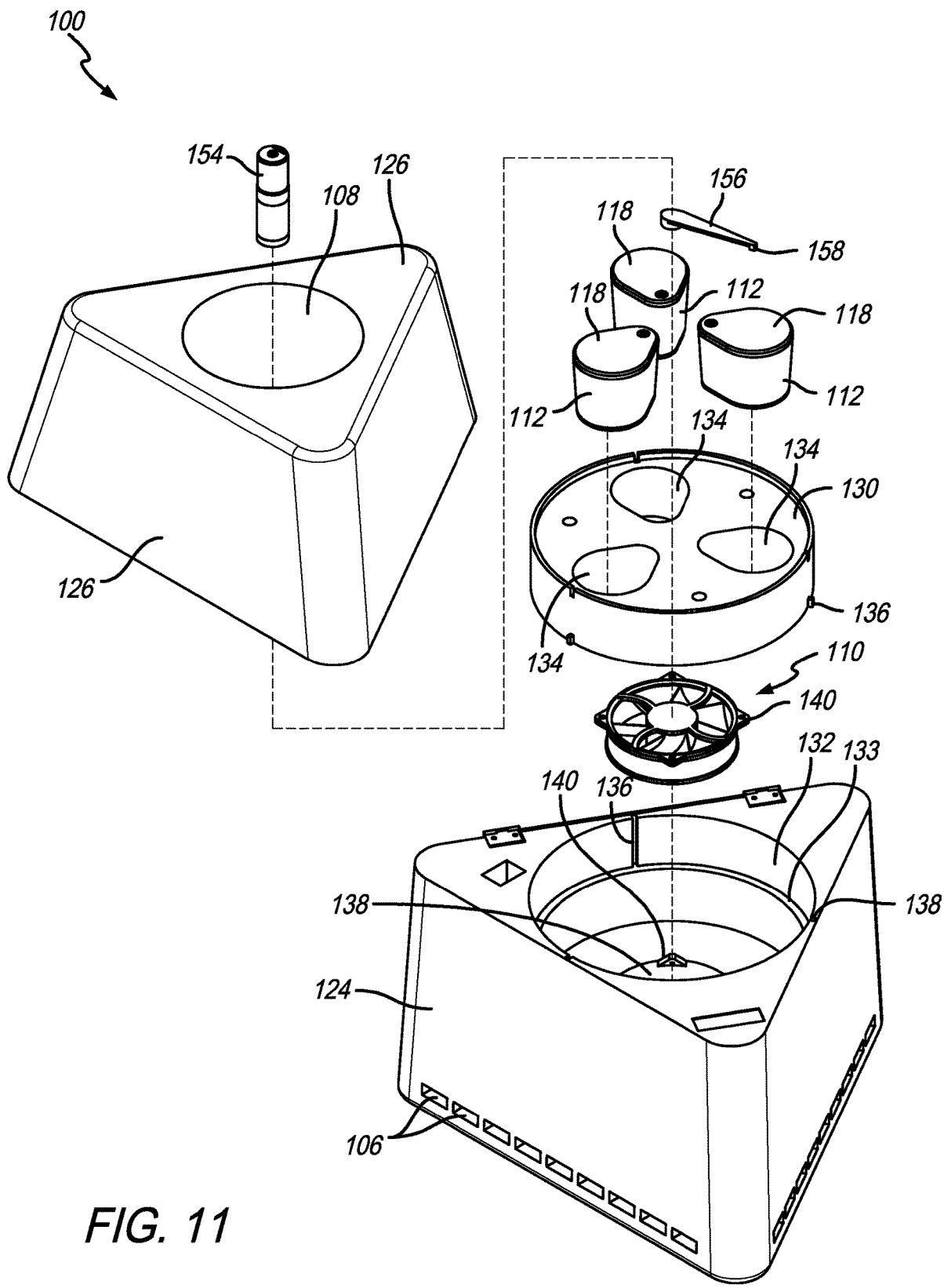
FIG. 11 is an exploded perspective view of the scent delivery assembly of FIG. 9.
Figure 12:
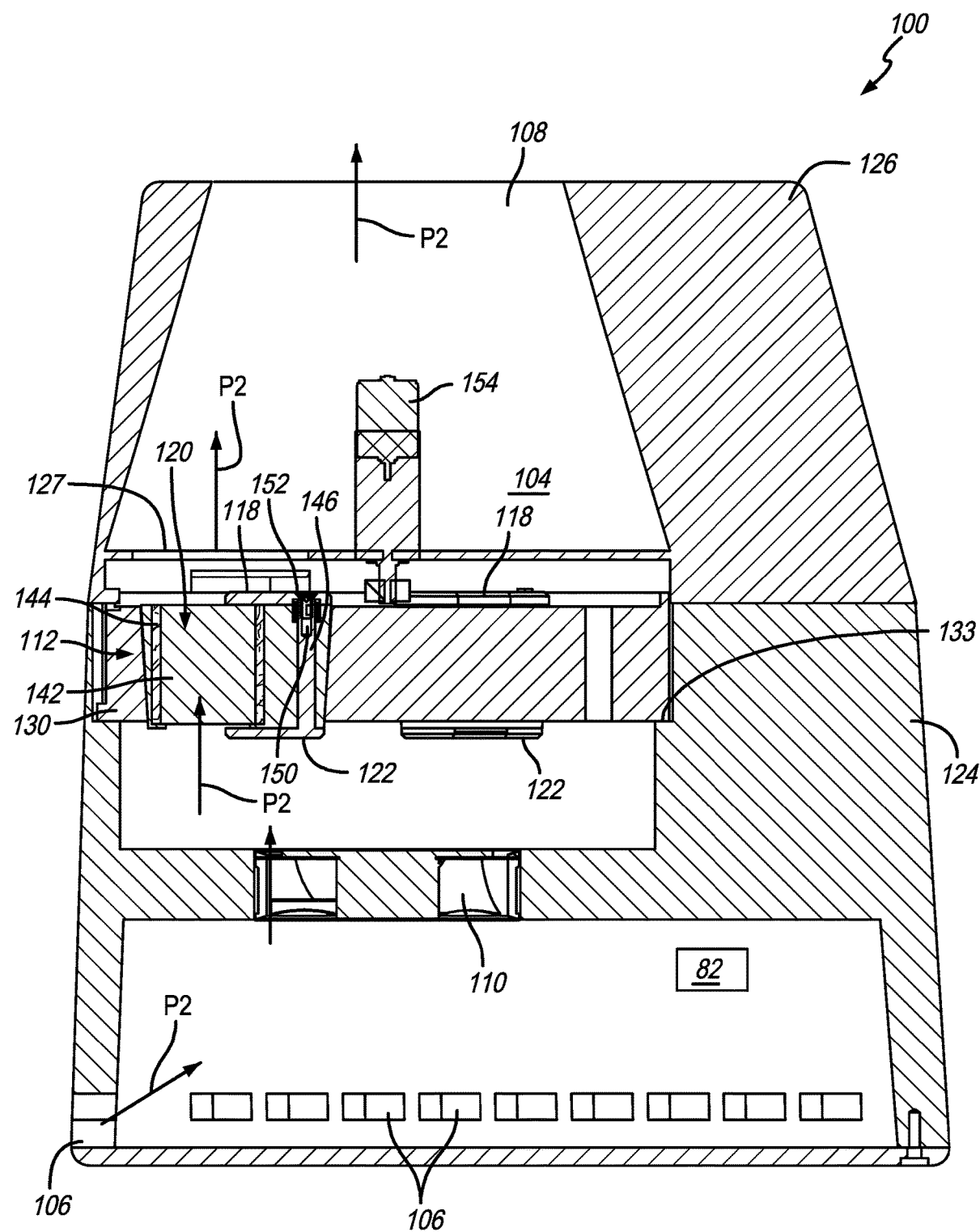
FIG. 12 is a cross-section of the scent delivery assembly of FIG. 9.
Figure 13:
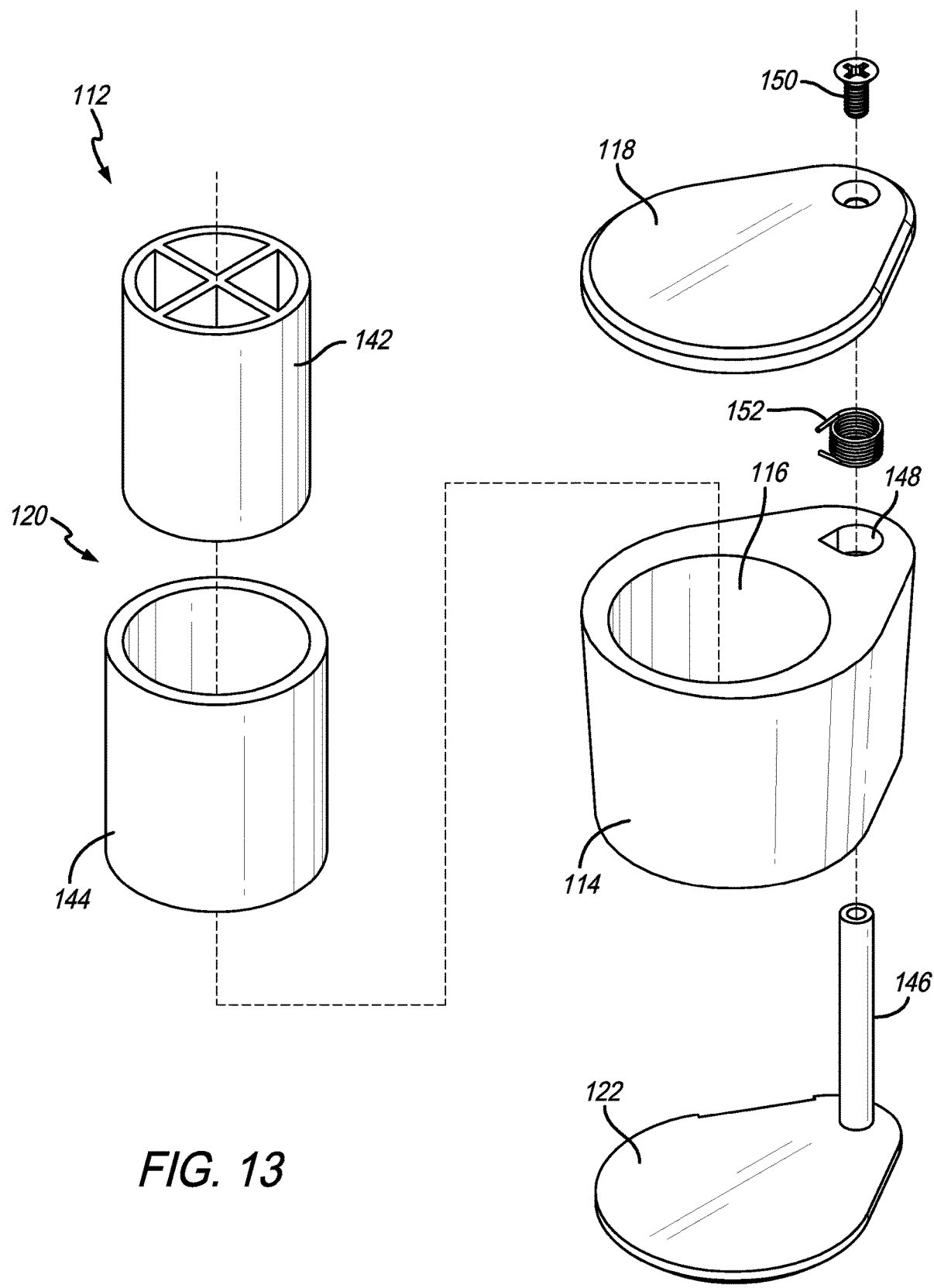
FIG. 13 is an exploded perspective view of a cartridge from the scent delivery assembly of FIG. 9.

With reference to FIGS. 9-13, scent delivery assembly 100 is shown and described. In a preferred embodiment, scent delivery assembly 100 includes a main body portion 102 that defines an interior 104 and includes at least one intake opening 106 and at least one outlet opening 108. As shown in FIG. 12, an airflow path P2 is defined between the intake opening 106 and the outlet opening 108. A fan 110 is positioned along the airflow path P2. At least one and preferably a plurality of cartridges 112 are positioned along the airflow path P2. As shown in FIG. 13, each cartridge 112 includes a housing portion 114 that defines a housing interior 116, a first cover 118 and a scent assembly 120 positioned in the housing interior 116. The first cover 118 is movable between a closed position and an open position. In a preferred embodiment, the cartridge 112 includes a second cover 122 that is movable together with the first cover 118 between the closed position and the open position. It will be appreciated that the scent assembly 120 is positioned between the first cover 118 and the second cover 122 when the first and second covers are in the closed position and is therefore not in flow communication with the airflow path P2 when the first and second covers are in the closed position. The scent assembly 120 is in flow communication with the airflow path P2 when the first and second covers 118 and 122 are in the open position. FIG. 9 shows one cartridge 112 with the first cover 118 in the open position and the other two cartridges 112 with their first covers 118 in the closed position.

As shown in FIGS. 9-12, in a preferred embodiment, the main body portion 102 includes a lower housing portion 124 and an upper housing portion 126 that cooperate to define the interior 104. The intake openings 106 are is defined in the lower housing portion 124 and the outlet opening 108 is defined in the upper housing portion 126. Preferably, the upper housing portion 126 is hingedly connected (see hinges 128) to the lower housing portion 126. However, in another embodiment, the upper housing portion 126 can be removable. As shown in FIG. 10, the upper housing portion 126 includes openings 127 therein that are generally aligned with the cartridges 112.

As shown in FIGS. 9-12, the scent delivery assembly 100 includes a removable tray portion 130 that is received in a tray portion recess 132 that is defined in the lower housing portion 124 and includes a ledge 133. The tray portion 130 includes a plurality of cartridge openings 134 that receive the cartridges 112. In a preferred embodiment, the housing portion 114 of the cartridges 112 is tapered and the cartridge openings 134 include a similar taper to hold the cartridges in place (the taper can be seen in FIG. 12), and allows them to be removed and replaced. In a preferred embodiment, the tray portion 130 and tray portion recess 132 include complementary male and female alignment members 136. In the drawings, the male alignment member is shown in the tray portion 130 and the female alignment members are shown defined in the lower housing portion 124 in the tray portion recess 132. However, this arrangement can be reversed. The upper housing portion 126 also includes alignment members 136 for aligning with the tray portion 130 The fan 110 is positioned in an opening 138 in the lower housing portion 124. Preferably, the fan 110 includes tabs 140 that mate with complementary tabs 140 on the lower housing portion to position and secure the fan 110.

FIG. 13 best shows a cartridge 112. As shown, the cartridge 112 includes the housing 114, with the interior 116, which is preferably a cylindrical opening, first and second covers 118 and 122 and the scent assembly 120. Preferably, the scent assembly 120 includes an inner diffusing portion 142 and an outer reservoir portion 144. The second cover 122 (the lower cover) has a pivot shaft 146 extending therefrom that extends through a pivot opening 148 defined in the housing portion 114. The pivot shaft 146 is connected to the first cover 118 by a threaded fastener 150. Preferably, a spring 152 (e.g., a torsion spring) is received on the pivot shaft 146 and into the pivot opening 148 and biases the first and second covers 118 and 122 toward the closed position. In another embodiment, the pivot shaft 146 can extend from the first cover 118. In another embodiment, the pivot shaft 146 can be removably connected (via a threaded fastener or the like) to both the first and the second cover. Similar to the first embodiment, the cartridges 112 reseal when closed to keep scent from diffusing therefrom.

As shown in FIGS. 9-11, in a preferred embodiment, the scent delivery assembly includes a motor 154 that is operable to move the first cover 118 (and, therefore, the second cover 122) between the open and closed positions. The motor 154 includes an arm 156 extending therefrom that includes a finger 158 on the distal end thereof. The motor 154 can move the arm in a rotational manner. In use, when the arm 156 rotates the finger 158 contacts the first cover 118 of a cartridge 112 and pivots the first cover 118 to the open position. To close the first cover 118, the arm 156 continues to rotate in the same direction, and, because of the curved shape of the first cover 118, once the arm 156 passes the first cover 118, the spring 152 biases the first cover 118 back to the closed position. Because the first cover 118 is connected to the second cover 122 via the shaft 146, the second cover 122 always pivots with the first cover 118. In another embodiment, the arm can rotate the opposite direction (of the opening direction) to allow the cover to close.

Similar to the embodiment described above, the scent delivery assembly 100 includes a controller 82 that controls the motor 154 and thereby the opening and closing of the first and second covers. The controller also controls the operation of the fan.

In use, when a user wants to diffuse a scent into the environment, the user pushes a button or the like on the tablet or other control panel. The tablet communicates with the controller 82 of the scent delivery assembly 10, which, in turn, actuates the motor 154. The motor 154 rotates the arm 156 such that the first cover 118 of the appropriate cartridge 112 is pivoted to the open position. Because shaft 146 is attached to second cover 122, the second cover 122 is also moved to the open position. This opens the scent assembly 120 to the airflow path P2. The controller 82 also actuates fan 110, thereby pulling air through intake openings 106 and moving air along airflow path P2. As a result of air flowing over the exposed diffusing portion 142, oil is pulled from the reservoir portion 144, is expelled through outlet opening 108 and released into the environment.

FIGS. 14-30 show another embodiment of a scent deliver assembly or fragrance dispensing unit 310 in accordance with a preferred embodiment of the present invention. The fragrance dispensing unit 310 includes one or more fragrance modules 312 therein. The fragrance modules 312 are each configured to receive a fragrance cartridge 314. The present invention also includes a method or system for using or integrating a plurality of fragrance dispensing units 310 within one or more zones in an aircraft.

Figure 14:
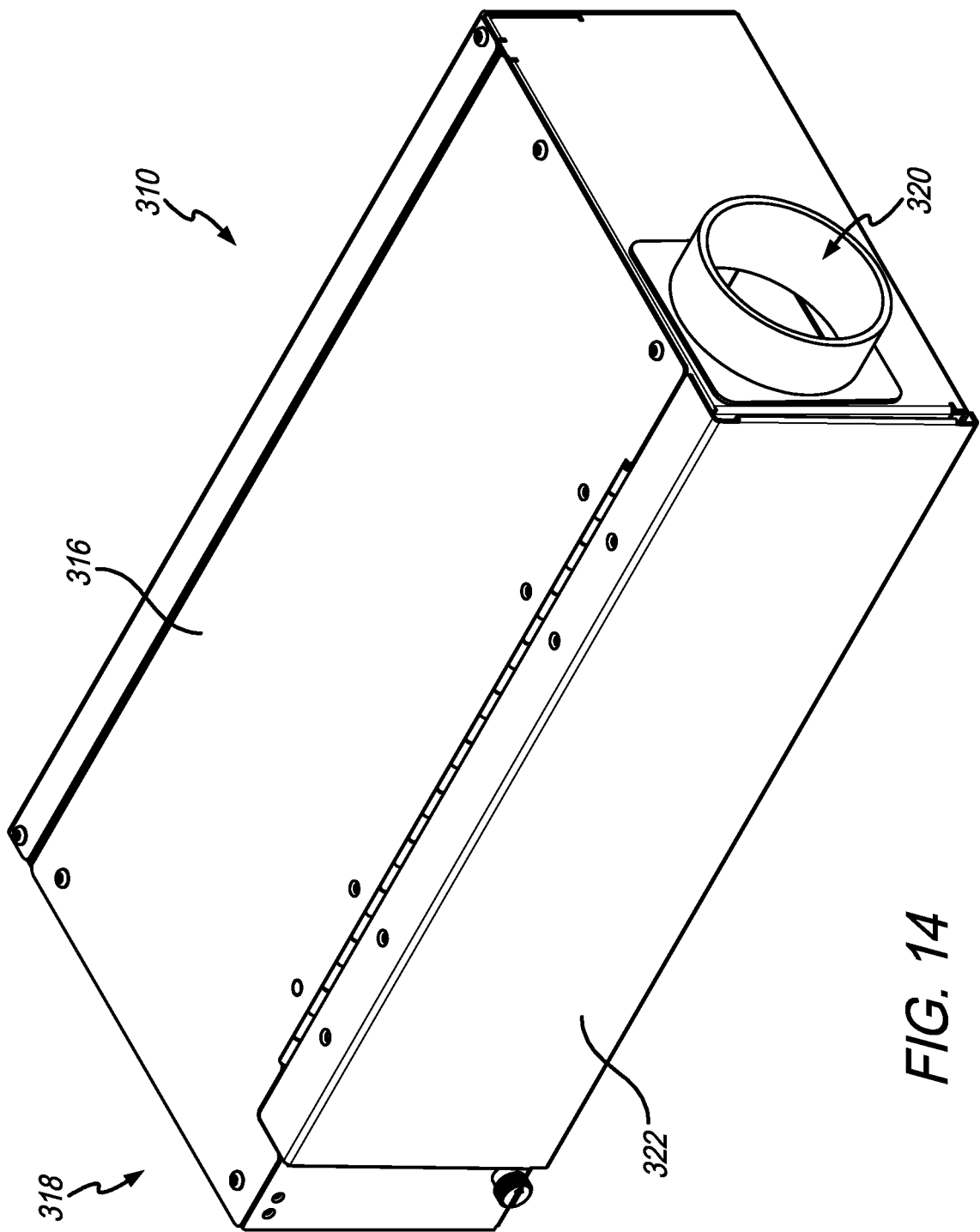
FIG. 14 is a perspective view of a fragrance dispensing unit in accordance with a preferred embodiment of the present invention.
Figure 15:
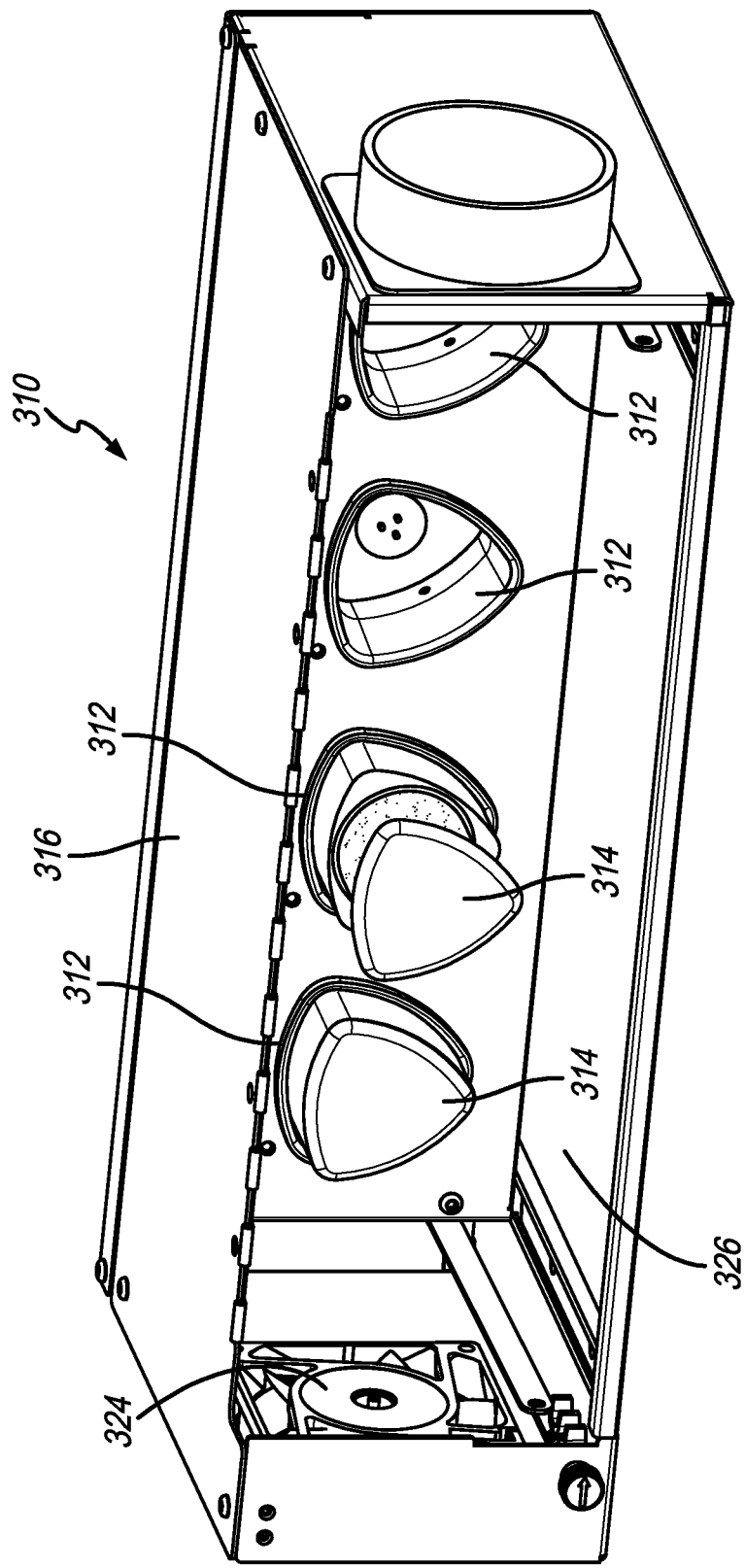
FIG. 15 is a perspective view of the fragrance dispensing unit of FIG. 14 with the door removed.

The fragrance dispensing unit 310 is best shown in FIGS. 14-15. As shown in FIG. 14, in a preferred embodiment, the fragrance dispensing unit 310 includes a housing 316 with an inlet 318, an outlet 320 and a cover or door 322 that is pivotally connected to the housing 316. FIG. 15 shows the dispensing unit 310 without the door 322. As shown, the interior of the housing 316 includes a plurality of fragrance modules 312, a fan 324 for pulling air into the housing interior, and a tray 326. The fragrance modules 312 are disposed on the tray 326, which is movable out of the front of the housing so that the fragrance cartridges 314 (two are shown in FIG. 15, one in the open position and one in the closed position) can be replaced or the fragrance modules 312 can be removed. In other words, the tray 326 is movable between an open and a closed position. It will be appreciated that the fragrance dispensing unit 310 can include as few as one fragrance module 312 or more than four fragrance modules 312. Any number of fragrance modules within a single fragrance dispensing unit 310 is within the scope of the present invention.

In a preferred embodiment, the fragrance dispensing unit 310 is designed to contain any flames or fire within the housing. In a preferred embodiment, a flame arrester (not shown) is positioned in the interior and adjacent the outlet 320. Any type of flame arrester can be used. For example, the flame arrester can be a heat exchanger that draws heat out of flame and disperses it along the housing. This type of flame arrester includes a steel honeycomb that the air goes through and is cooled to extinguish any flame.

Figure 16:
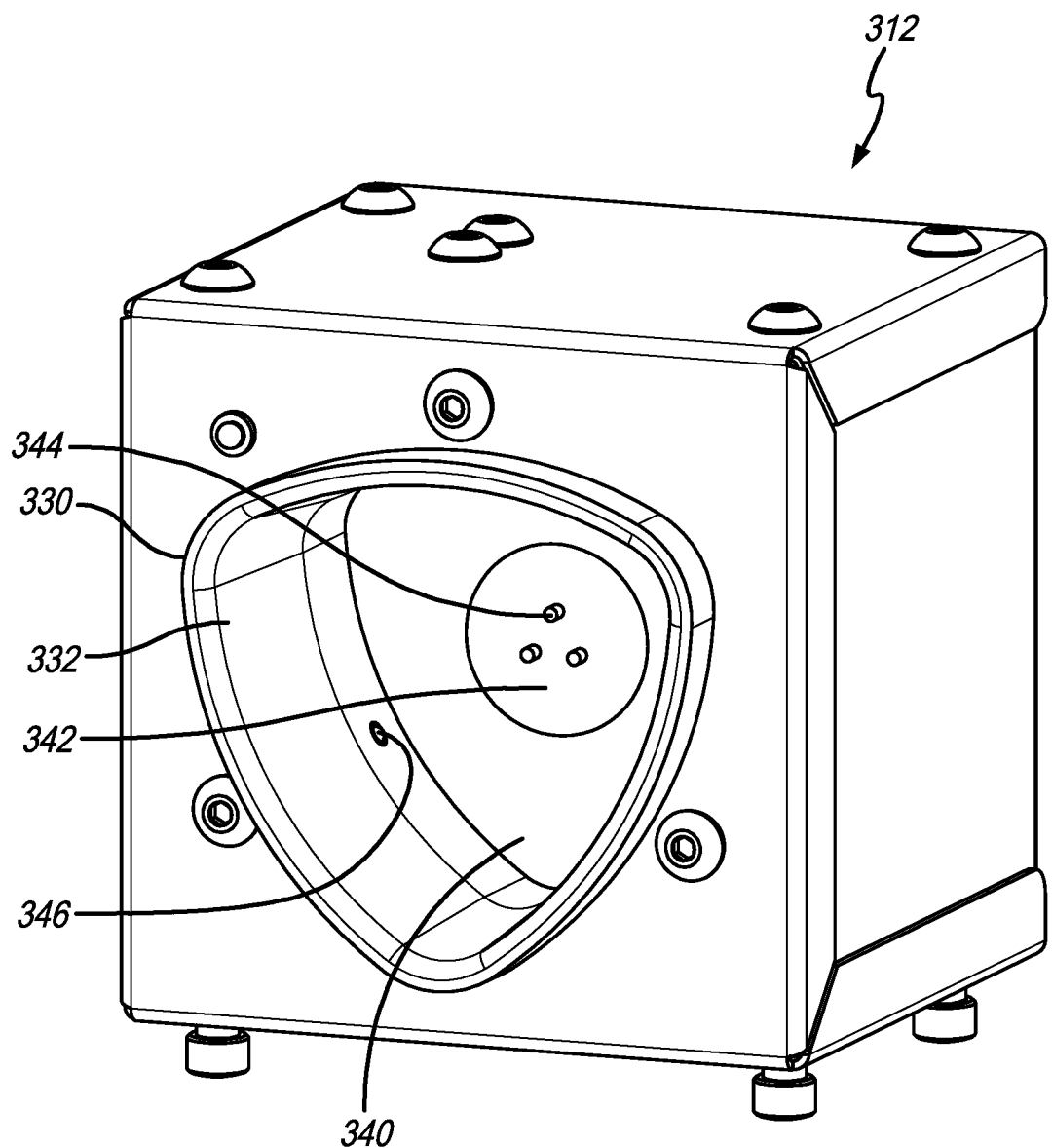
FIG. 16 is a perspective view of a fragrance module in accordance with a preferred embodiment of the present invention.
Figure 17:
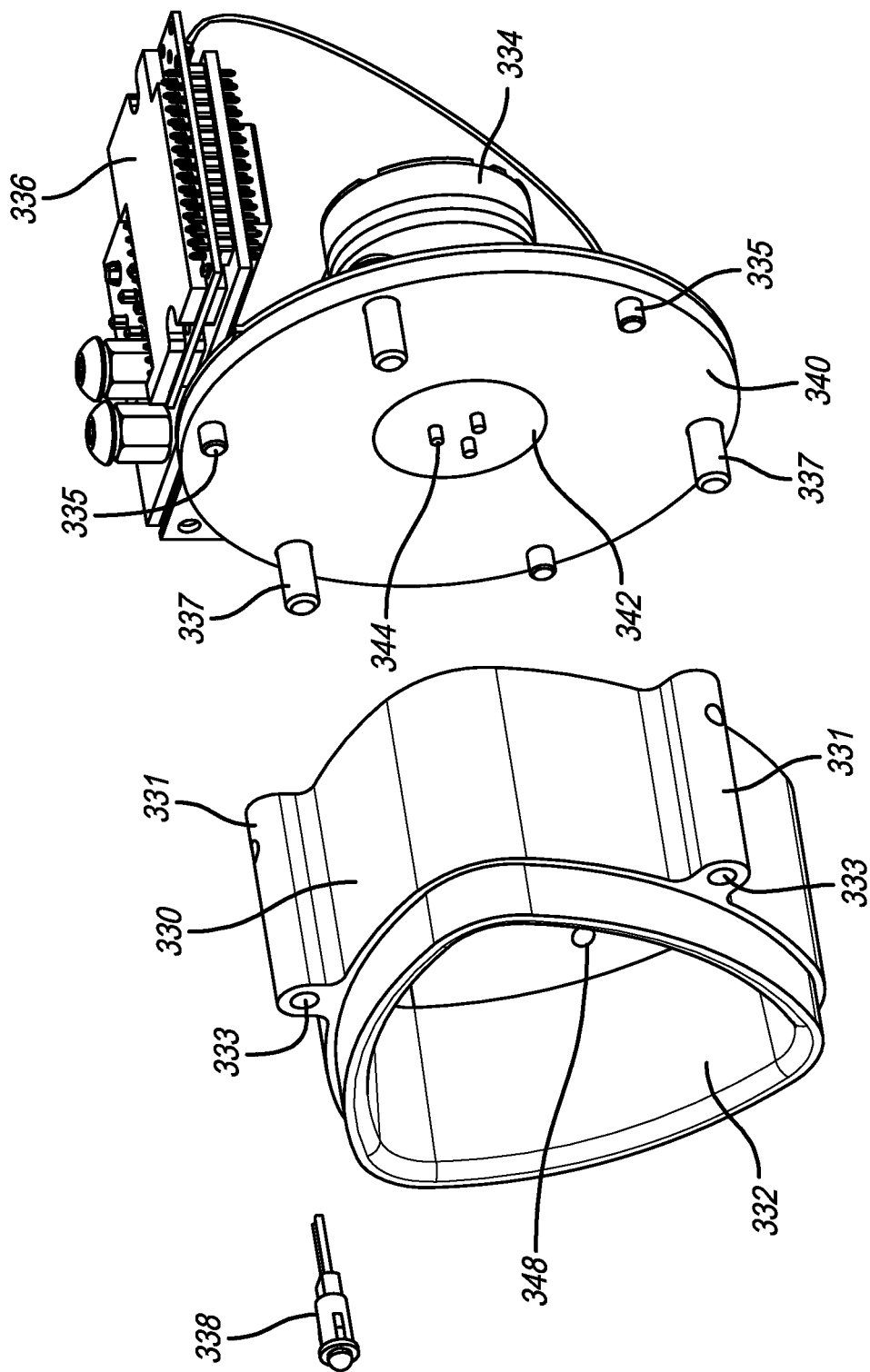
FIG. 17 is an exploded perspective view of the interior of the fragrance module of FIG. 16 with the housing removed.
Figure 18:
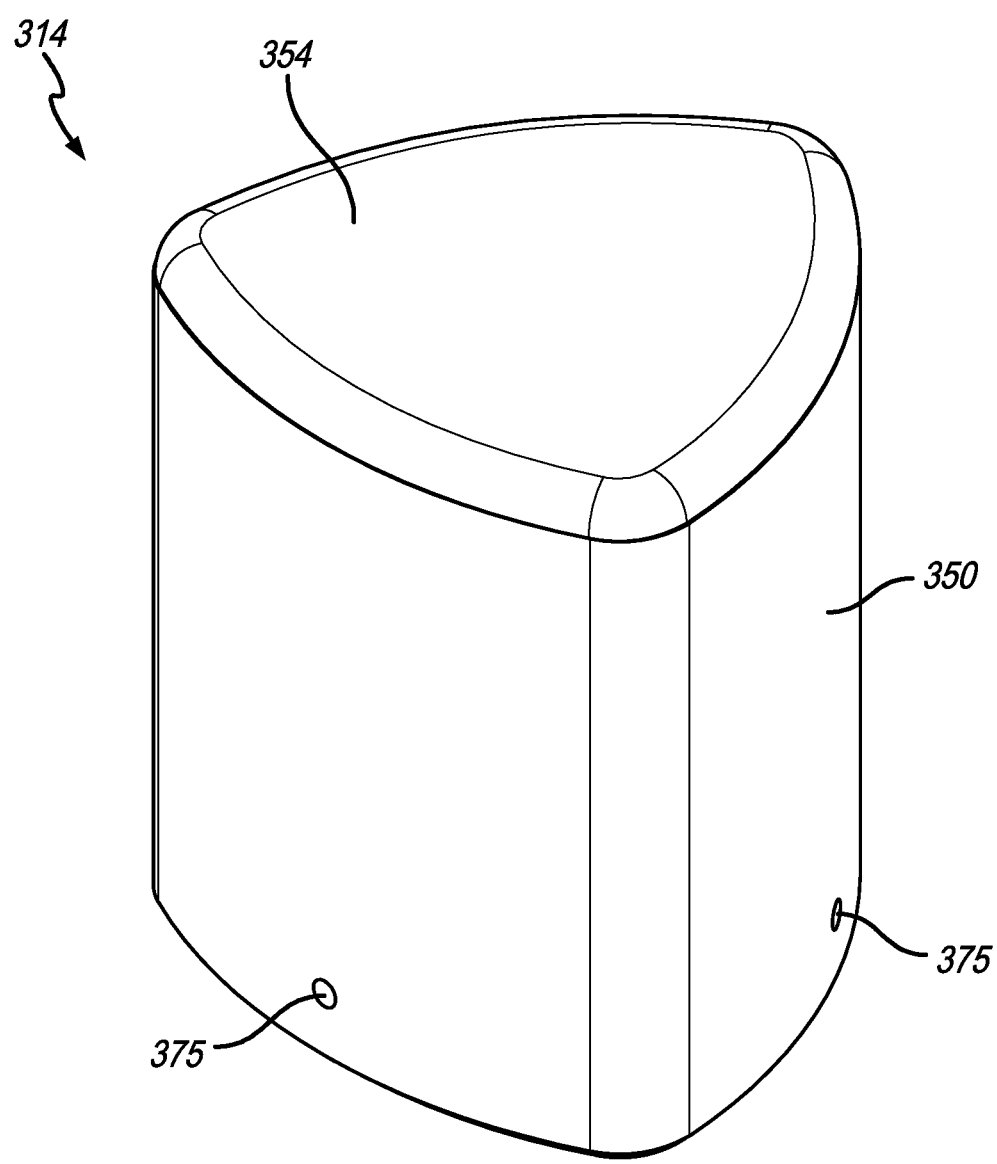
FIG. 18 is a perspective view of a fragrance cartridge in accordance with a preferred embodiment of the present invention.

FIGS. 16 and 17 show a fragrance module 312. As shown in FIG. 16, the fragrance module 312 includes a housing 328 and a cartridge enclosure 330 that includes an opening 332 for receiving a fragrance cartridge 314 (not shown in FIGS. 16 and 17). FIG. 17 shows an exploded view of the interior of the fragrance module 312 with the housing omitted. As shown, the interior includes a motor 334, a PCB 336 in communication with the motor 334, the cartridge enclosure 330, an LED 338 and a base 340. In a preferred embodiment, the motor 334 is a DC motor. However, this is not a limitation on the present invention. The base 340 includes a rotatable plate 342 having a plurality of protrusions 344 extending outwardly therefrom. As described more fully below, the protrusions 344 engage with slots on the fragrance cartridge 314. In use, the motor 334 rotates the rotatable plate 342 and protrusions 344 to rotate a component in the fragrance cartridge 314 to open the fragrance cartridge 314 to expose the scent assembly. The scent assembly can be any component that includes the ability to wick away a scent. In a preferred embodiment, the scent assembly is taught in U.S. Pat. No. 7,651,077, the entirety of which is incorporated by reference herein.

In a preferred embodiment, the cartridge enclosure 330 includes a plurality of balls or protrusions 346 that are biased inwardly into the module interior. The protrusions 346 cooperate with and are seated in indentations or dimples 375 defined in or on the outside of the cartridge 314. Therefore, when the cartridge 314 is loaded into the module 312 through the front opening 332 and into the module interior, the protrusions 346 are biased (by a spring or the like) into the indentations. In a preferred embodiment, the protrusions are ball bearings that are partially pressed through openings 348 in the cartridge enclosure 330 by a spring.

Preferably, the cartridge enclosure 330 includes connection protrusions 331 extending outwardly therefrom and that include openings 333 defined therein. The openings 333 receive posts 335 extends outwardly from the base 340. Long threaded fasteners (not shown) are received in the front opening 333 and extend into an opening in post 335 to secure the cartridge enclosure 330 on the base 340. The base 340 can also include threaded fasteners 337 that extend into openings in the back of the cartridge enclosure 330.

Figure 19:
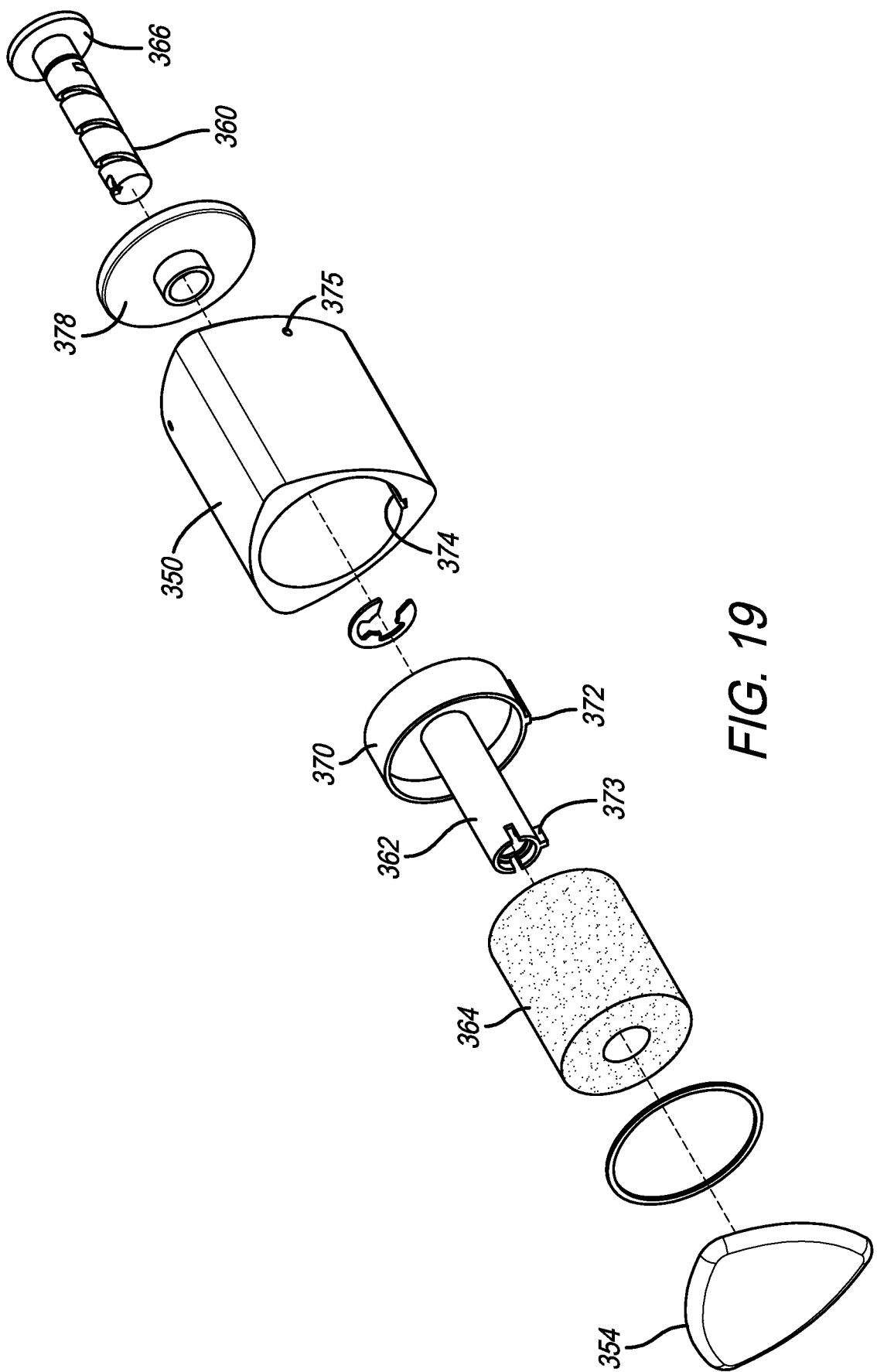
FIG. 19 is an exploded perspective view of the fragrance cartridge of FIG. 18.
Figure 20:
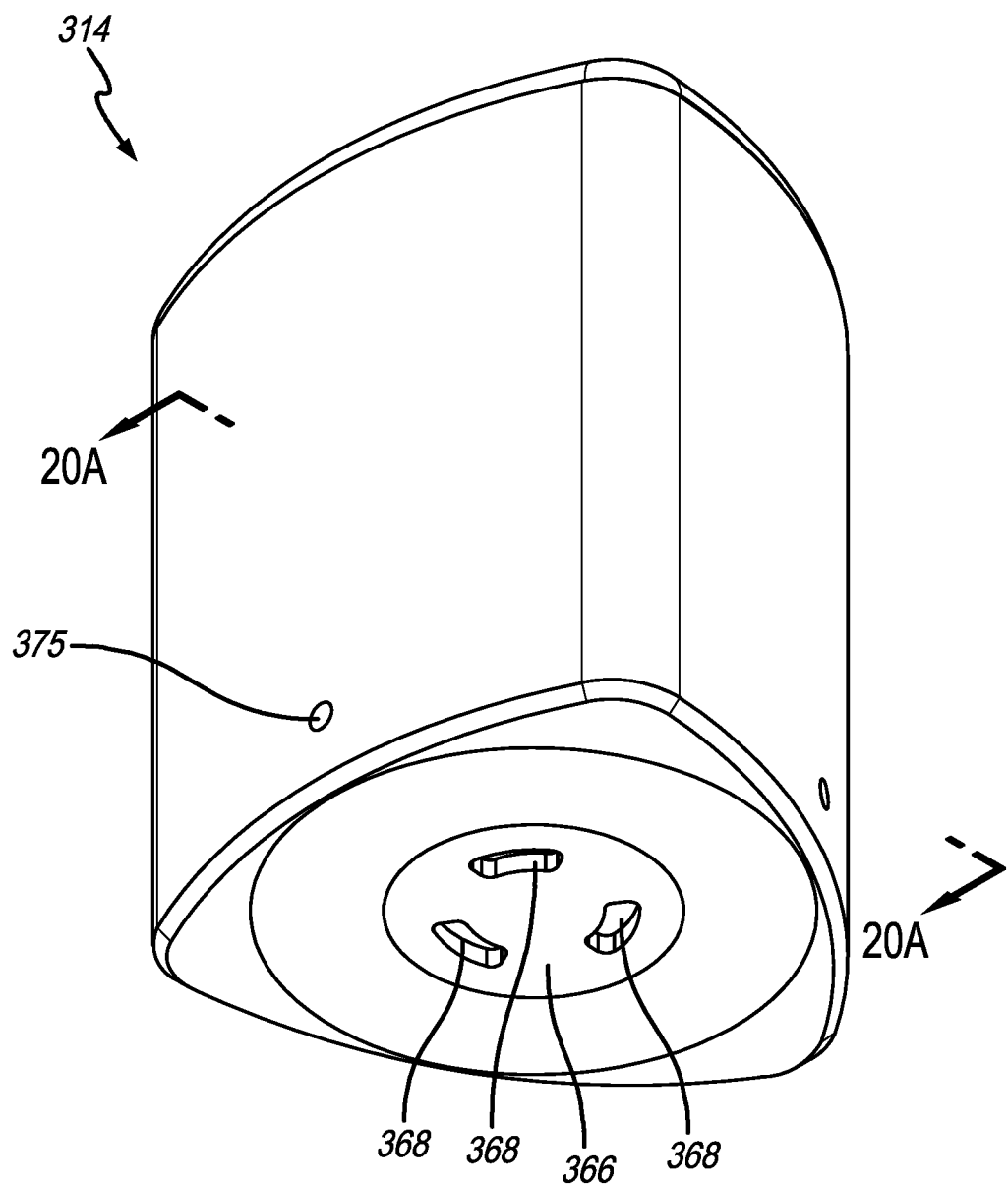
FIG. 20 is a perspective view of the fragrance cartridge in the closed position.
Figure 20A:
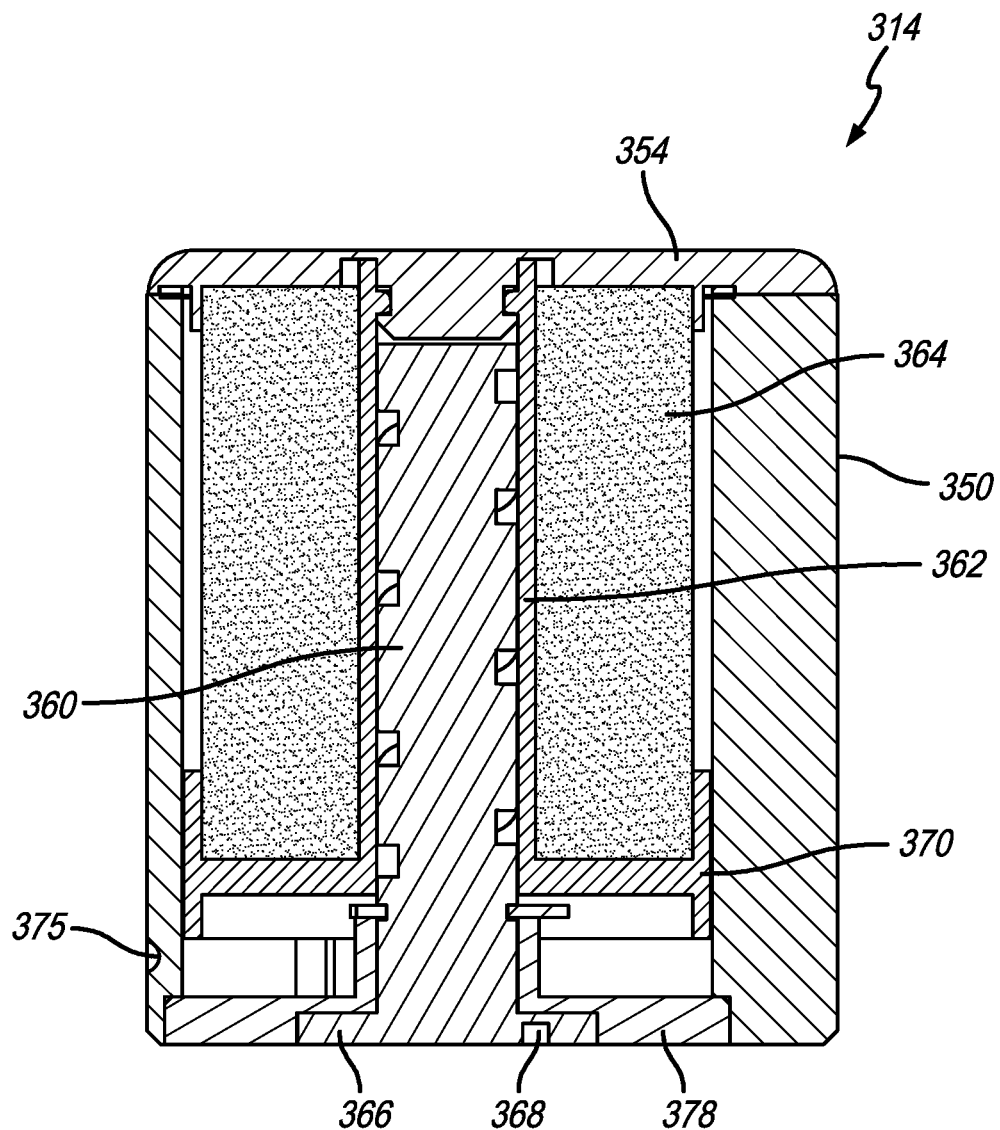
FIG. 20A is a cross-sectional view of the fragrance cartridge in the closed position taken along line 20A-20A in FIG. 20.
Figure 21:
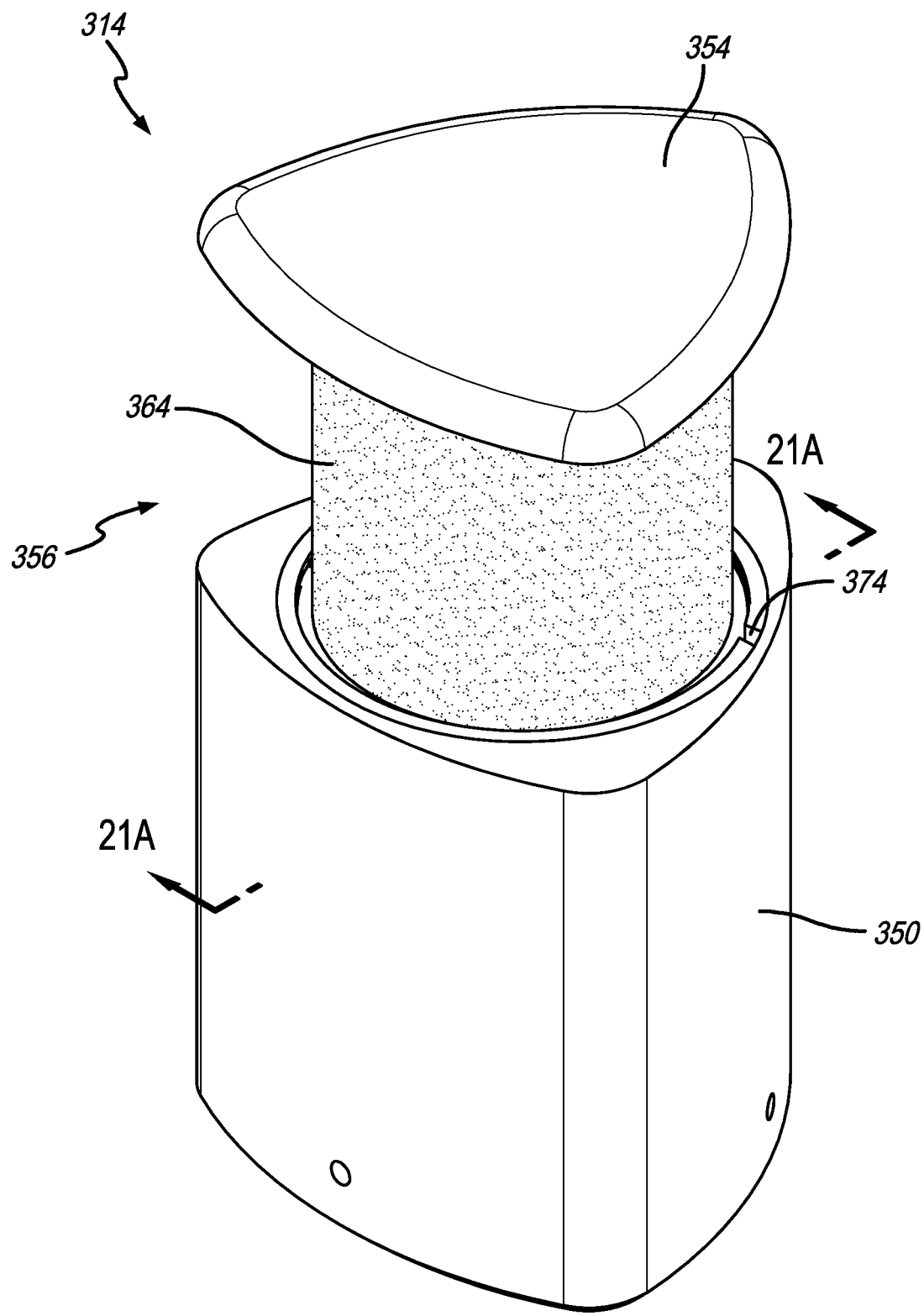
FIG. 21 is a perspective view of the fragrance cartridge in the open position taken along line 21A-21A in FIG. 21.
Figure 21A:
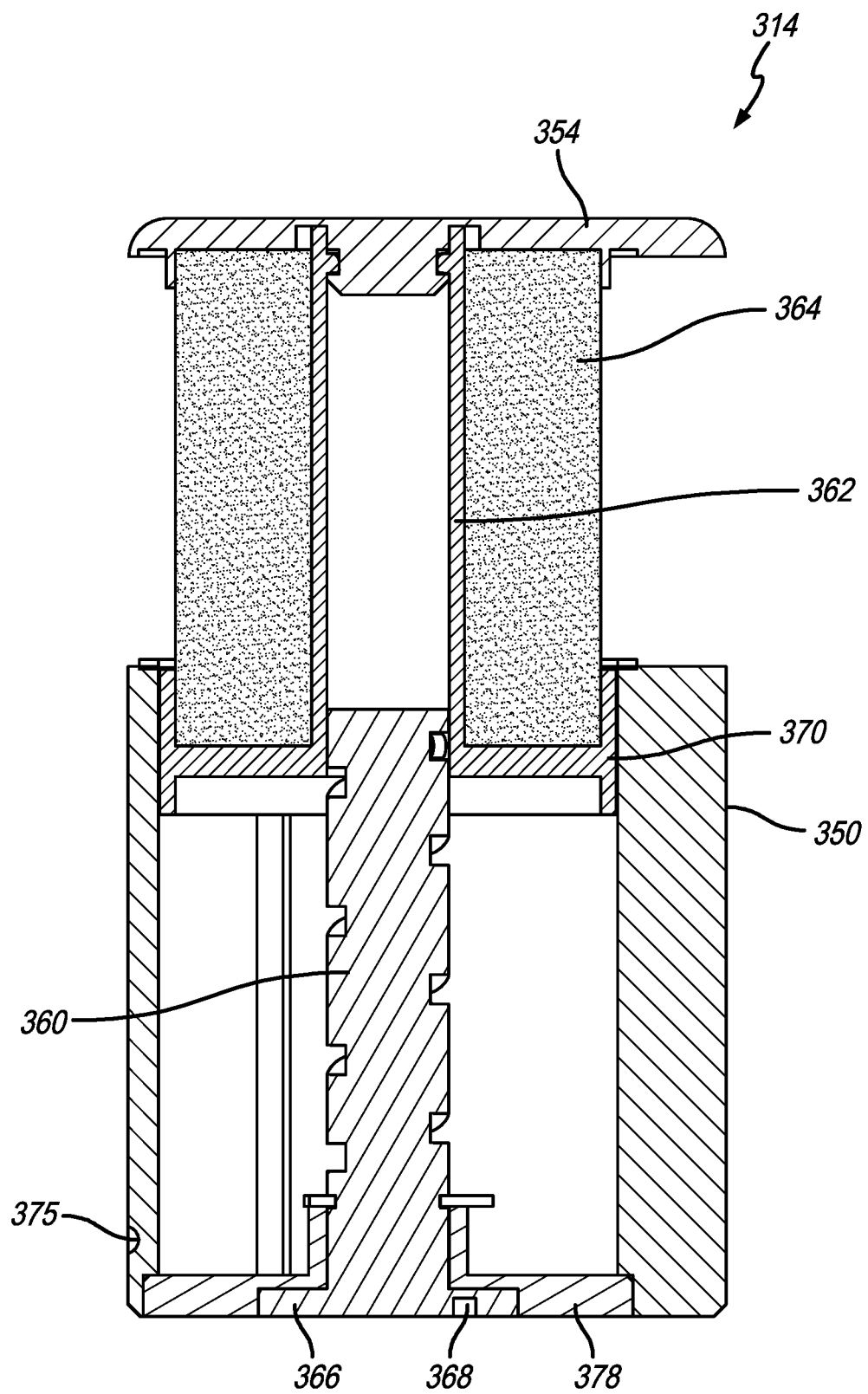
FIG. 21A is a cross-sectional view of the fragrance cartridge in the open position.
Figure 22:
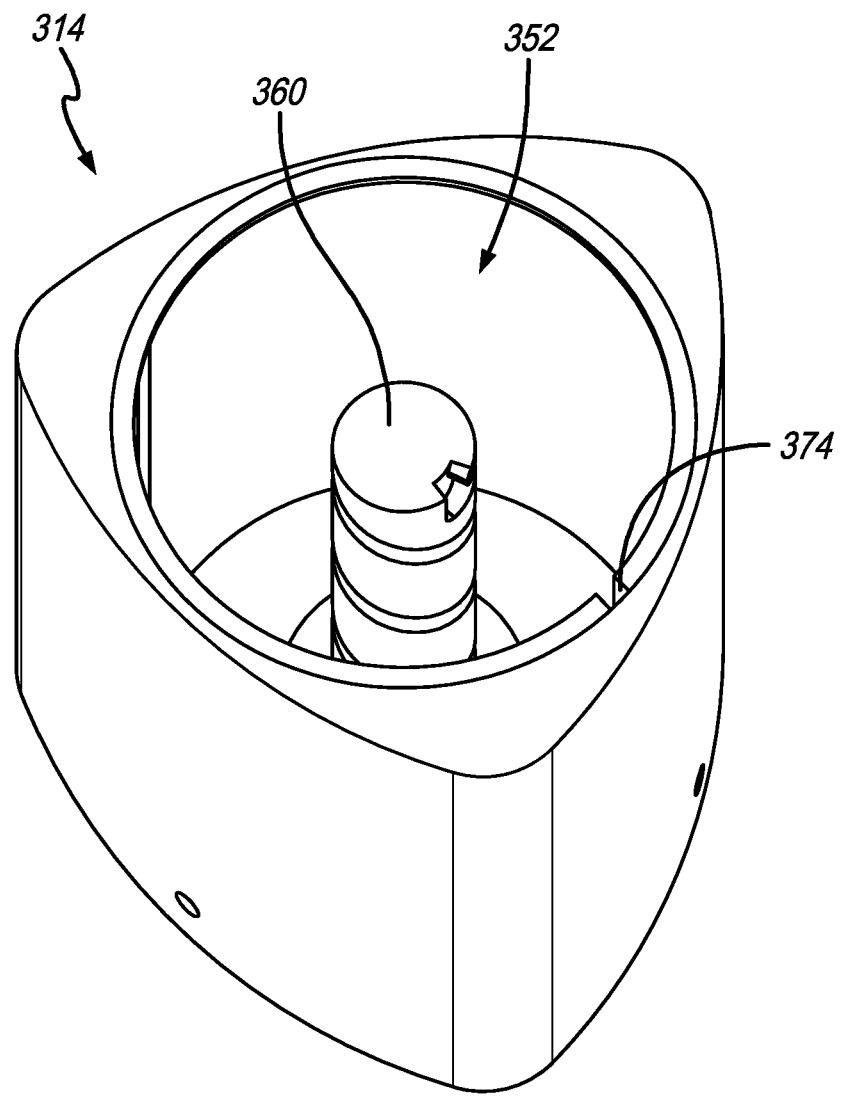
FIG. 22 is a perspective view of the interior of the fragrance cartridge with the scent assembly removed.

FIGS. 18-23 show the fragrance cartridge 314, which is received in the module interior of the fragrance module 312. As shown, in a preferred embodiment, the cartridge 314 is shaped to fit into the cartridge enclosure 330 in the module 312. As shown in FIG. 19, the cartridge 314 generally includes a housing portion 350 that defines a housing interior 352, a cover 354, a movable scent assembly 356, and a communication portion 358. The movable scent assembly 356 includes an exteriorly threaded post 360 with female threads and an interiorly threaded cylinder 362 with male threads. The opposite threading arrangement can be used. The scent assembly 356 also includes a wick or scented portion 364. The threaded engagement of the post 360 and cylinder 362 allow the cylinder 362, on which the scented portion 364 is mounted, together with the cover 354 to move between a closed position and an open position. Rotational motion of the rotatable plate 342 is translated to linear or axial motion of the scented portion 364.

Figure 23:
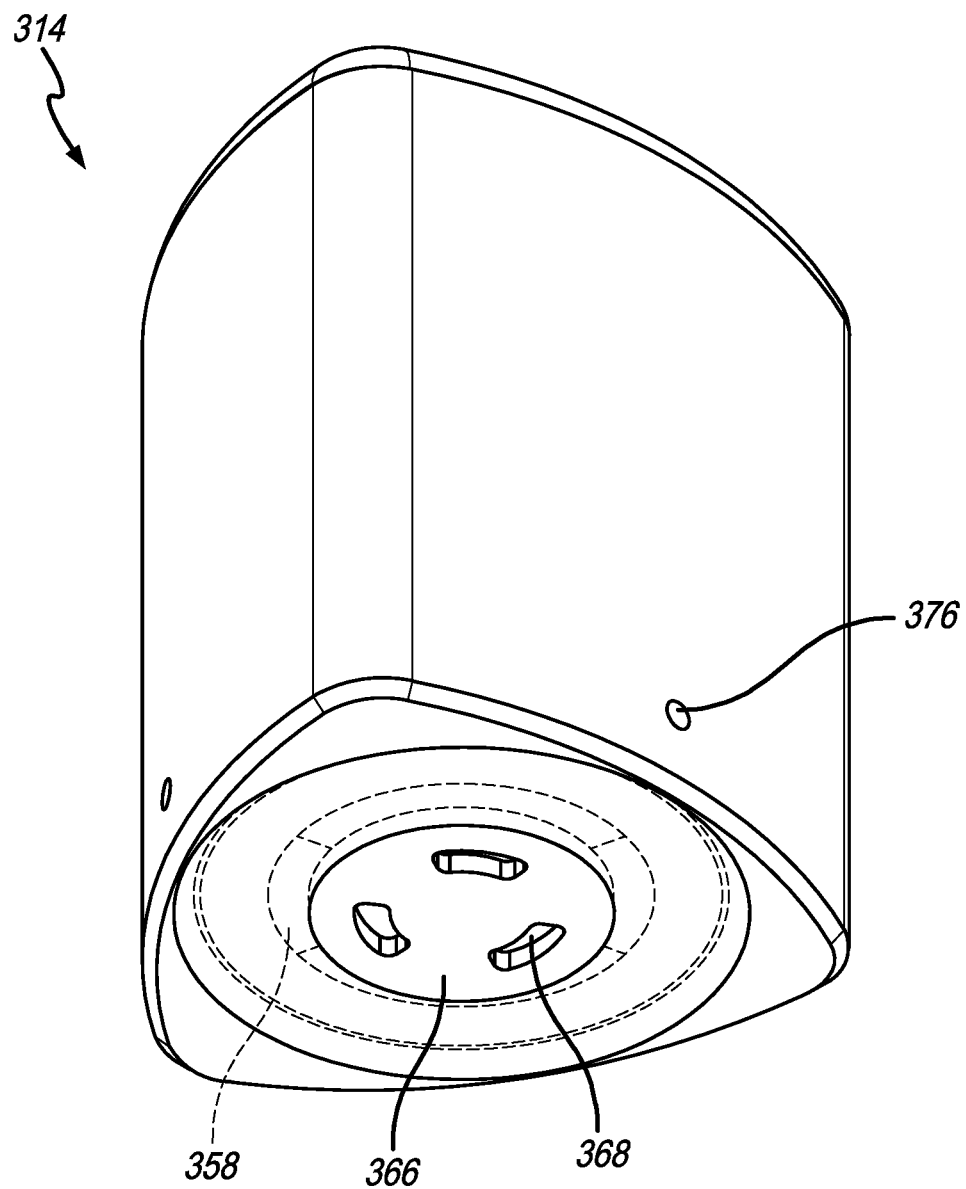
FIG. 23 is a bottom perspective view of the fragrance cartridge with the communication portion shown in hidden lines.

As shown in FIG. 23, the threaded post 360 includes a disk 366 on the bottom thereof that has slots 368 defined therein. These slots 368 receive the protrusions 344 in the module 312. Therefore, when the motor 334 turns the rotatable plate 342 and protrusions 344, as a result of the engagement of the protrusions 344 and the slots 368, the post 360 is rotated. Then, as a result of the engagement of the threads on the post 360 and cylinder 362 the post 360, scented portion 364 and cover 354 move outwardly to the open position and to expose the scented portion 364. Rotation of the rotatable plate 342 and protrusions 344 in the opposite direction causes the components to move to the closed position. In a preferred embodiment, the protrusions 344 are spring-loaded outwardly so that when the cartridge 314 is inserted into the module 312, but the slots 368 are not properly aligned, the protrusions 344 are pushed up into the slots 368 after proper alignment. However this is not a limitation on the present invention.

In a preferred embodiment, the fragrance technology is dry dispersion. As will be appreciated by those of ordinary skill in the art, the oils are evaporated by air being blown across a wetted wick (scent portion 364). In a preferred embodiment, the scent portion 364 includes an inner reservoir that holds the scented oil and an outer diffusing portion, similar to scent portion 30 above. The dry fragrances are dispersed in molecular form and preferably leave little to no residue on surfaces. The dry type preferably results in a high dispersion rate of the fragrance in cabin environment.

In a preferred embodiment, the distal end of the rotatable cylinder 362 is received in a recess in the bottom of the cover 354 and includes a key 373 that is received in a corresponding slot. Preferably, the rotatable cylinder 362 also includes a base 370 that seats the scented portion 364. Preferably, the base 370 includes a key or protrusion 372 that is received in a slot 374 defined in the interior of the housing portion 350. The arrangement between the protrusions 372 and slot 374 help keep the components in alignment when moving between the open and closed positions. The indentations 376, described above, that cooperate with the protrusions 346 in the module 312 are shown in FIGS. 19-23.

In a preferred embodiment, the cartridge 314 includes near field communication technology (NFC) that communicates with NFC in the module 312, the FDU 310 or other component. As shown in FIG. 23, preferably, the NFC chip or the like is housed in the communication portion 358 and is positioned behind a bottom cover 378.

Figure 24:
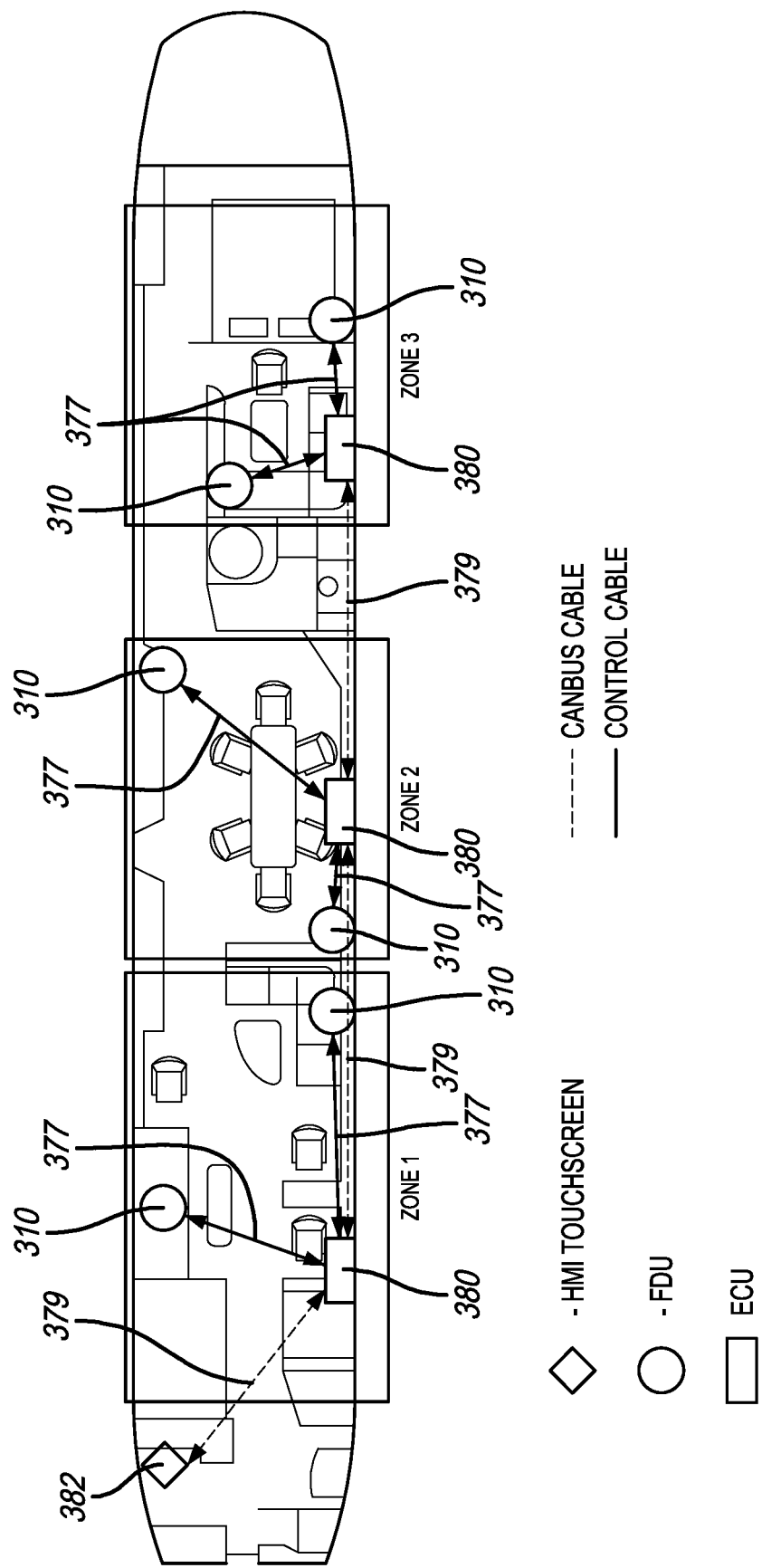
FIG. 24 is a top plan view of an aircraft with a plurality of zones therein.
Figure 25:
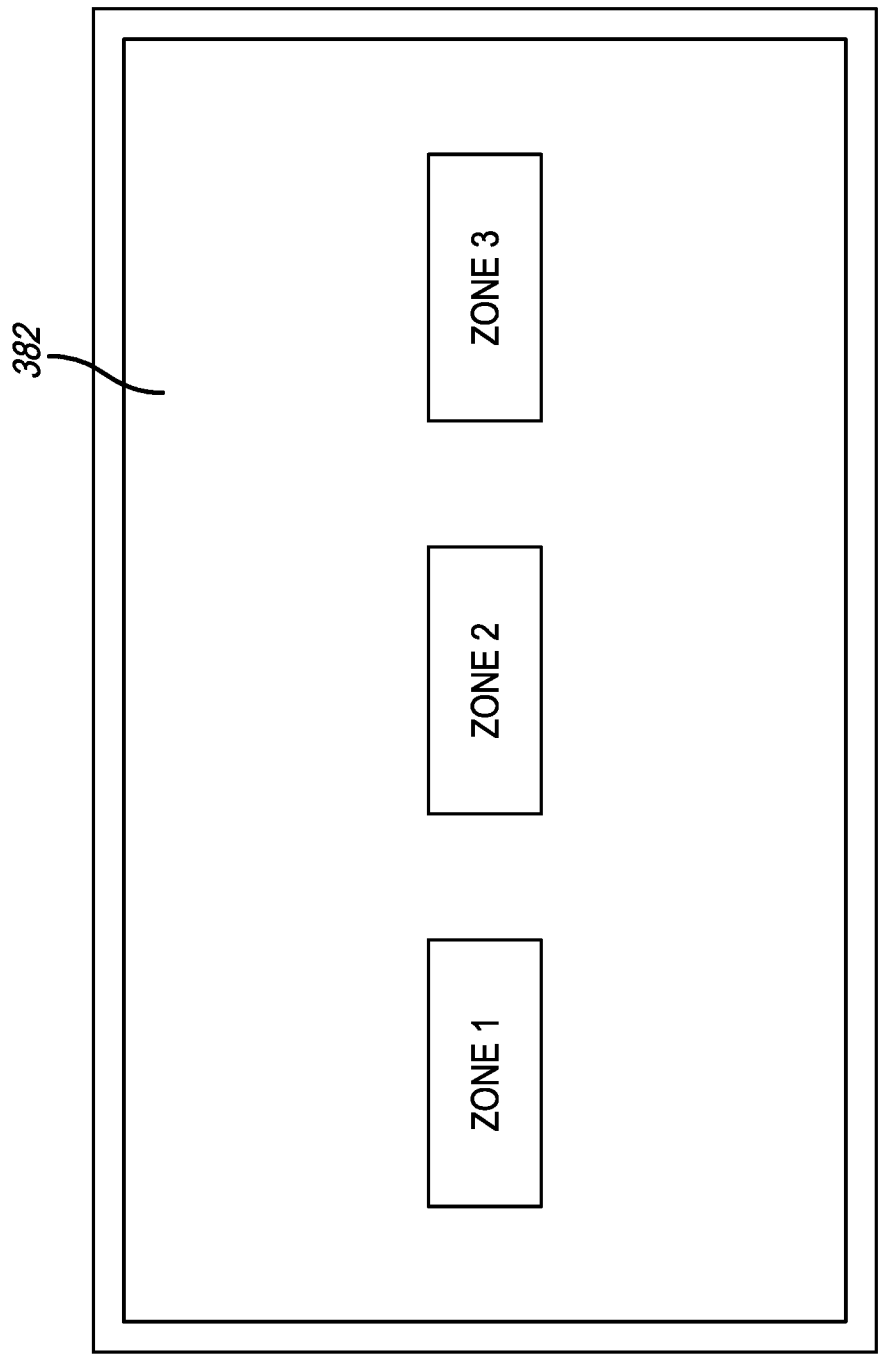
FIG. 25 is an illustration of an exemplary screen on the touchscreen of the present invention showing the zone choices.
Figure 26:
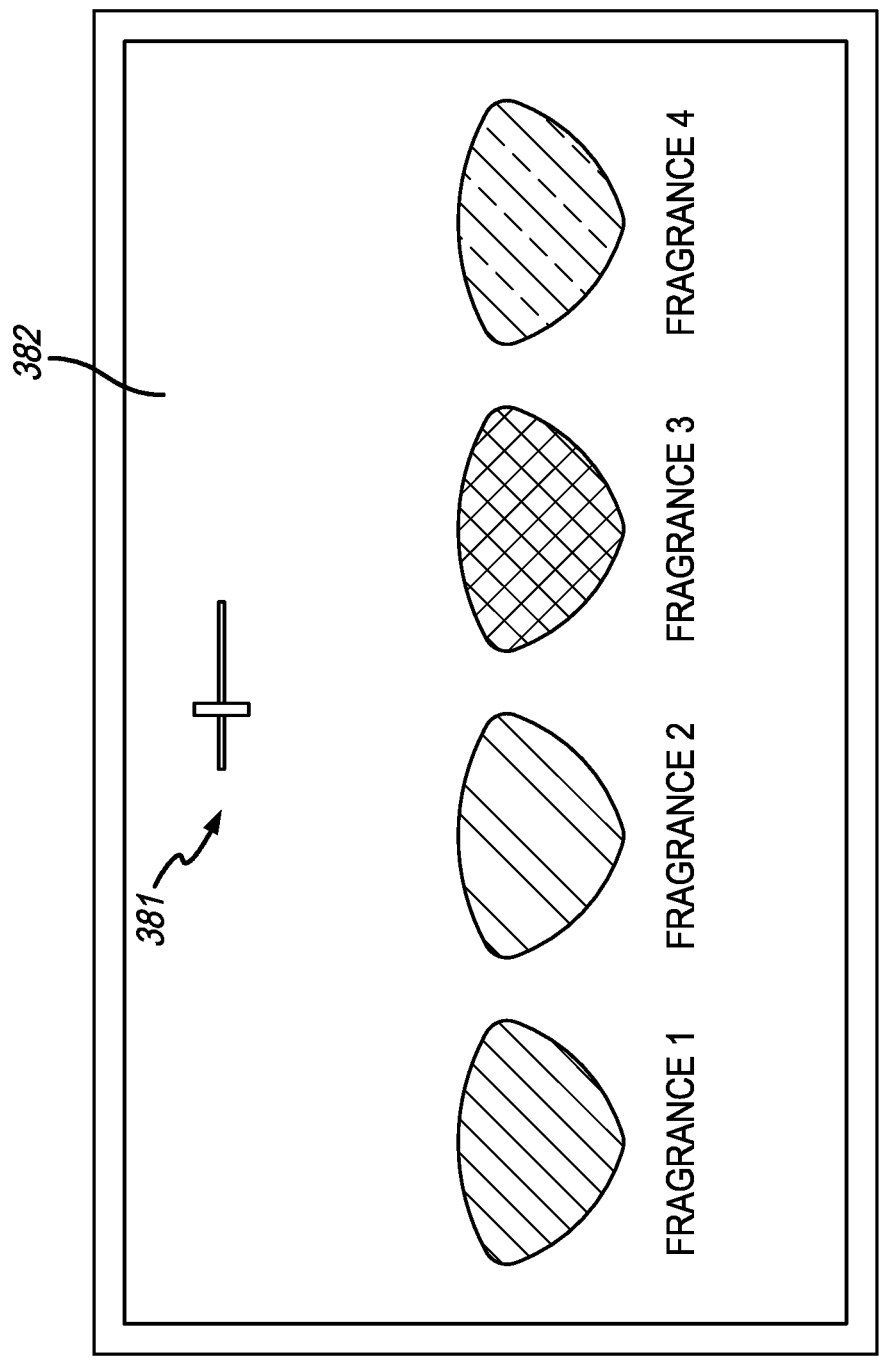
FIG. 26 is an illustration of an exemplary screen on the touchscreen of the present invention showing four fragrance choices (corresponding to a fragrance dispensing unit with four modules and cartridges therein)
Figure 27:
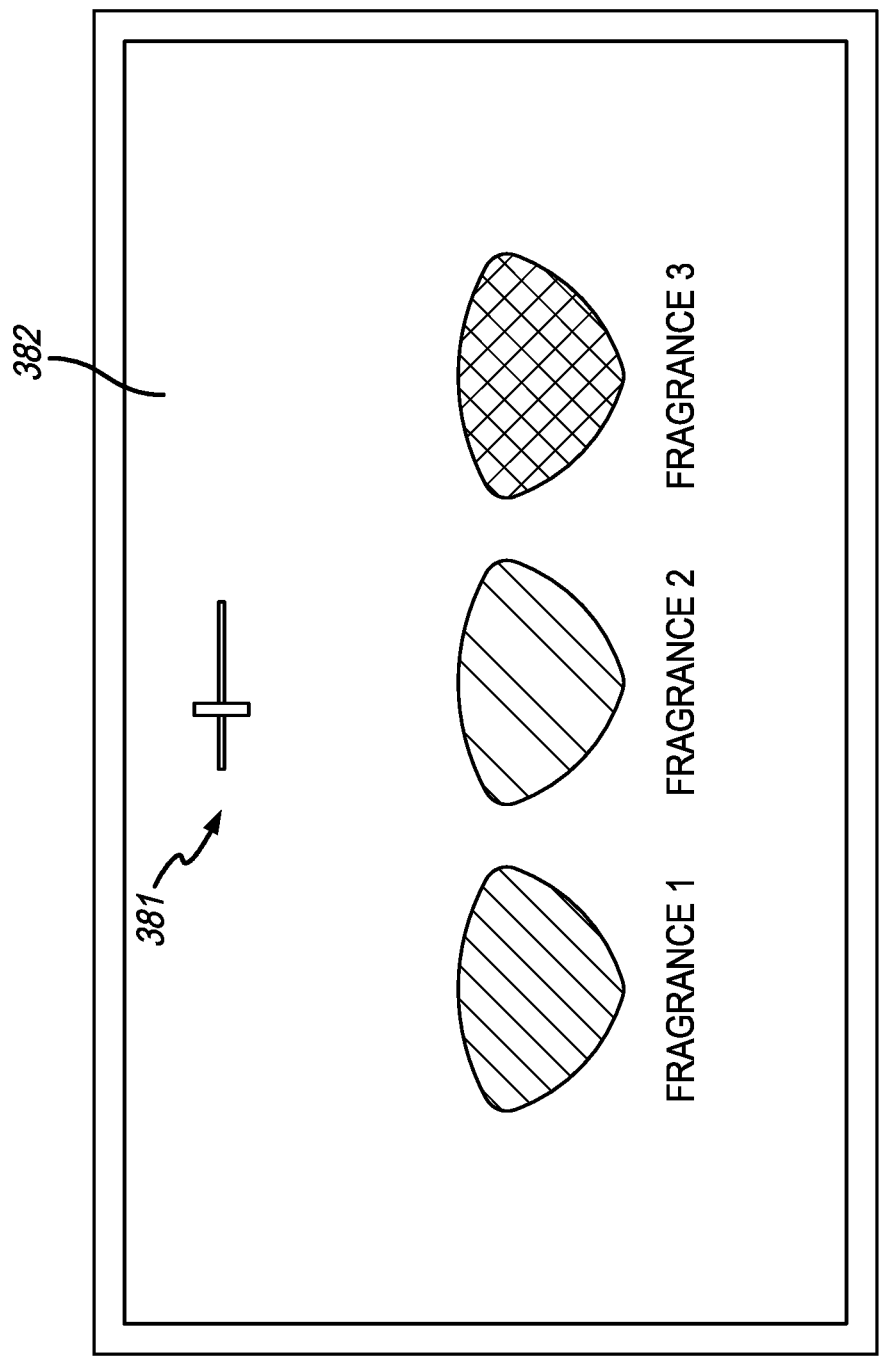
FIG. 27 is an illustration of an exemplary screen on the touchscreen of the present invention showing three fragrance choices (corresponding to a fragrance dispensing unit with three modules and cartridges therein)
Figure 28:
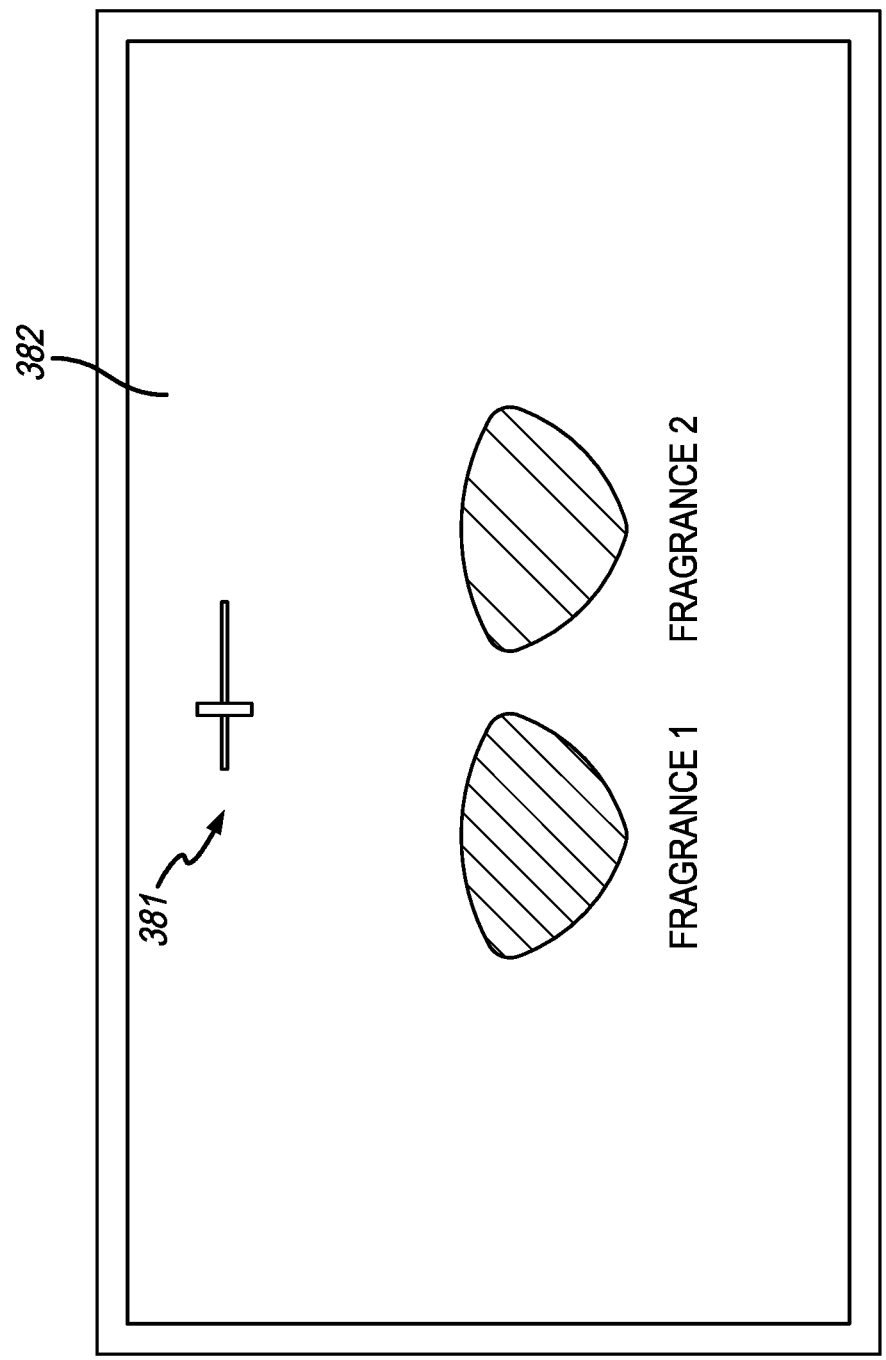
FIG. 28 is an illustration of an exemplary screen on the touchscreen of the present invention showing two fragrance choices (corresponding to a fragrance dispensing unit with two modules and cartridges therein)
Figure 29:
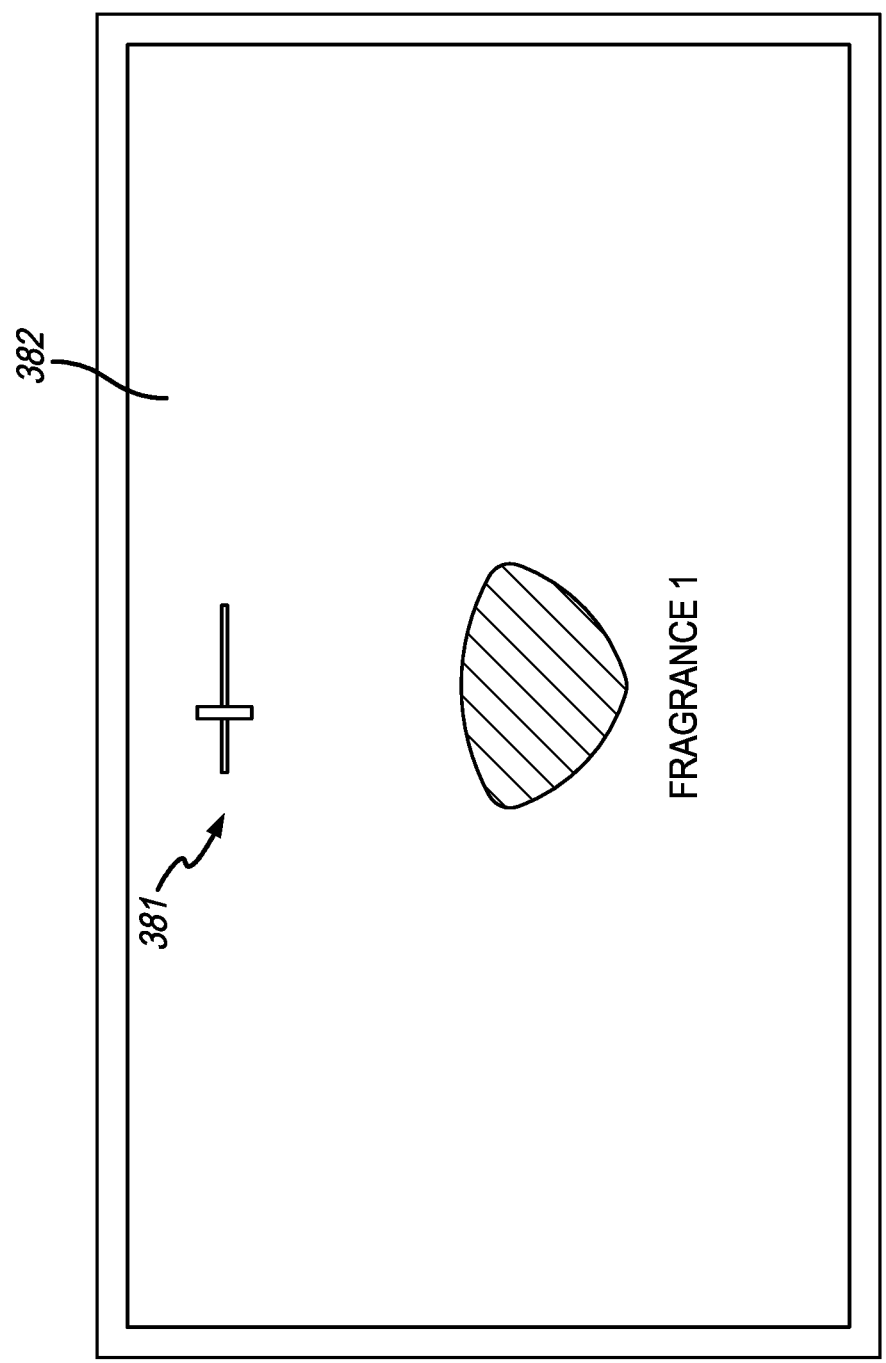
FIG. 29 is an illustration of an exemplary screen on the touchscreen of the present invention showing one fragrance choices (corresponding to a fragrance dispensing unit with one module and cartridge therein)

FIG. 24 shows a LOPA (layout of passenger accommodation) of a VIP aircraft that includes three zones (zone 1, zone 2 and zone 3). Within each zone is an electronic control unit 380 (ECU) that contains most of the electrical components of the system for the zone (and can be mounted on a wall or the like) and two fragrance dispensing units 310 (FDU). The fragrance dispensing units 310 communicate with the ECU 380 via a control cable 377 (or any wired connection) (they can also communicate wirelessly). The control units 380 communicate with one another and with a user interface device or HMI touch screen 382 via a CAN Bus data cable 379 (or any wired connection) (they can also communicate wirelessly). The user interface device 382 can be any device that includes buttons (touchscreen or analog) or other controls for allowing a user to turn the fragrance dispersion on or off, up or down, etc. In another embodiment, the user interface device can be integrated with or be a part of a central command unit on the aircraft that controls other features such as lights, temperature and entertainment. It will be appreciated that each zone can include a single FDU or two or more FDUs. In a preferred embodiment, the ECU includes the motor drivers for activating the motors 334 in the fragrance modules 312. In another embodiment, the stand alone It will be appreciated by those of ordinary skill in the art that in a preferred embodiment of the present invention, the system includes smart cartridge technology (NFC encoding) and user error proofing (fragrance cross checking), it is modular and configurable for each custom aircraft, includes multiple fragrances, individually controlled zones, a central system control, each zone can be locally controlled, replaceable cartridges 314, dry scent technology, wired/wireless interface. In another embodiment, the system does not include NFC encoding.

The system of the present invention allows the deliverability of customized fragrances throughout the aircraft environment. As shown in FIG. 24, each zone is controlled locally by the ECU. However, in another embodiment, each zone, and each FDU within a zone, can be controlled by a central control system or they can each be controlled separately. In other words, the control system can control multiple cabin zones.

As discussed above, the fragrance dispersion units 310 each contain single or multiple fragrance modules 312. If multiple fragrance modules 312 are included within an FDU, each module may contain a different fragrance, or all the modules may contain the same fragrance.

FIGS. 25-29 show an exemplary embodiment of the graphical user interface on the controller or touchscreen 382 that is in communication with the one or more ECUs 380. It will be appreciated that this same graphical user interface can be included on the individual ECUs 380 as well. The fragrance cartridges 314 each contain the near field communication (NFC) chip which is encoded with information such as the name of the fragrance, the manufacturing date, a unique identifier, and a color code (unique to a fragrance) or any combination of one or more of these features. The NFC chip communicates with the NFC antenna or coil in the fragrance module 312, which, in turn, communicates the encoded information to the associated ECU 380. The fragrance name and color code are used to display information for the user on the GUI 382, as shown in FIG. 26-29. The manufacturing date is communicated to monitor shelf life and cartridge usage life to the controller. Usage life is limited to ensure the quality of the fragrance throughout its life. The data is preferably encrypted to make the cartridge tamper resistant. However, in another embodiment it may not be encrypted. The controller keeps track of which fragrance cartridges are installed in each FDU or each zone if multiple FDU's are installed in a common zone.

In a preferred embodiment, the fragrance module 312 contains the drive motor 334 to open the cartridge 314 and an NFC reader, receiver, antenna or coil (can be part of the PCB 336) to decode the NFC chip once the cartridge 314 is inserted into the fragrance module 312. Information is then transmitted from the NFC chip, to the NFC reader and to the controller or controllers (ECU) which recognize the cartridge as new or in use and then displays it as an available fragrance on the touchscreen.

In a preferred embodiment, the controller utilizes a user friendly GUI on the touch-screen device for human interaction. The controller software maps all the available fragrances in each aircraft zone in its memory, which can be accessed through a series of menus. To activate a fragrance, the user selects an aircraft zone (see FIG. 25) and is presented with a list of available fragrances for that zone (e.g., see any of FIGS. 26-29). Upon selection of the desired fragrance, the controller commands the FDU or FDUs in the selected zone to open the fragrance cartridge and operate the fan for fragrance dispersion. In a preferred embodiment, the system also includes the ability to control the density of the fragrance released. As shown in FIGS. 26-29 (only numbered in FIG. 13) the touchscreen includes a slider bar 381 for increasing or decreasing the fragrance density.

In a preferred embodiment, the controller keeps track of the usage time for each cartridge, notifying the user when a cartridge should be replaced. A localized LED light 338 (see FIG. 17) on the module 312 or the FDU is used to help identify which cartridge is to be replaced. Furthermore, if a cartridge 314 is "empty" (the fragrance is all consumed), it will not be displayed on the controller or touchscreen. In a preferred embodiment, if a zone includes more than one FDU, each FDU includes the same scents or fragrances therein. In other words, if Fragrance 1 is included in the first FDU, but not in the second FDU, the controller will alert the user that there is an issue in that the fragrances do not match. However, if Fragrance 2 is located in both the first FDU and the second FDU, Fragrance 2 will appear as a choice on the controller or touchscreen for that zone. Therefore, only the fragrances that are in both FDUs are displayed for use. In another embodiment, the first and second FDUs can contain different fragrances.

Figure 30:
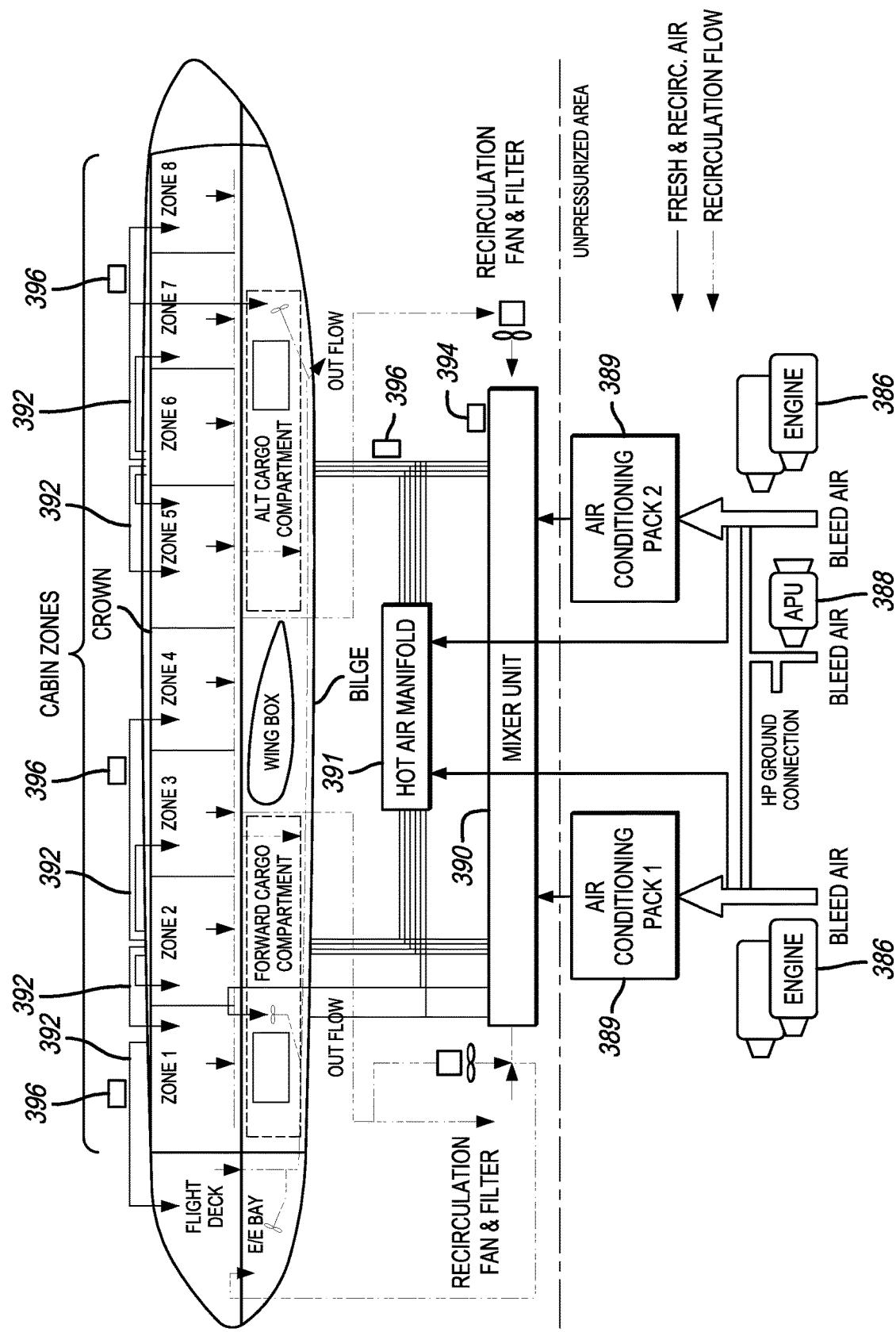
FIG. 30 is a schematic view of an aircraft environmental control system with the fragrance delivery system integrated therein.

FIG. 30 shows an environmental control system for a commercial aircraft 200 and how the fragrance dispensing system can be integrated into the ECS. The fragrance dispensing system taught herein can be integrated into the typical aircraft environmental control system (ECS) in any aircraft. In a typical ECS, compressed air is taken off the engines 386, the auxiliary power unit (APU) 388 or a ground cart (not shown). The air then goes through the air conditioning packs 389 to cool it through a process of compression and expansion cycles. There are filters and water separators in the A/C packs as well. From there, the air is fed into a mixer unit 390 where it is mixed with recirculated cabin air. For temperature control, the air is then fed through a hot air manifold or heat exchanger 391. An alternate method for temperature controls is to pump uncooled bleed air into the mixer unit as well. From there, the conditioned and temperature controlled air is fed into the cabin. There are different duct lines 392 for different zones in the cabin. The aircraft 200 in the exemplary embodiment includes eight passenger zones and the flight deck, as well as ducts leading to the cargo compartments. Some of the air that is displaced from the cabin is dumped overboard and some is recirculated back into the mixer unit.

In the present invention, fragrance can be delivered into the cabin in at least two ways using the ECS. The first is to inject the fragrance into the mixer unit 390 (see FDU 394 in FIG. 30). This yields evenly dispersed fragrance throughout the entire cabin. This scenario may be used by airlines and operators that are, for example, self-promoting their "scent brand" (i.e., passengers will associate the scent of the cabin with the airline).

In another embodiment, the fragrance can be introduced in the ducts 392 between the mixer unit 390 and the zones or cabin sections. This allows for fragrance scenting cabin areas independently (e.g., different classes can be scented differently). In this embodiment, the system shown in FIG. 24 can be used, except that the FDUs (see the exemplary FDUs 396 in FIG. 30) are positioned in or adjacent the ducts 392 to release fragrance into the ducts 392 as opposed to being located in a cabinet or other location within the zone.

To implement either of the systems discussed above (dispersion of fragrance in the mixing unit 390 or at some other point downstream of the ducts 392 for dispersion into the entire cabin or dispersion into separate ducts 392 for dispersion into zones), any of the scent delivery assemblies, fragrance dispensing units and/or systems can be used. For example, FDU 310 can be positioned in or in communication with the mixer unit 390 so that different scents can be dispersed into the mixer unit 390 and eventually into the cabin. FDU 310 can be in communication with a controller and/or a touch screen so that the scent dispersion from FDU 310 can be controlled from inside the cabin. In another embodiment, a different fragrance dispensing unit can be used, provided the ability to control the dispersion of one or more sense is included.

In another embodiment, a fragrance dispensing unit having one or more cartridges can be integrated into the personal service unit associated with each row or portion of a row of seats. This can provide control to individual passengers whether they are in a seat with others nearby or in their own room or suite.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

The teachings of the disclosure provided herein can be applied to other systems, not necessarily the system described above. The elements and acts of the various embodiments described above can be combined to provide further embodiments. Any measurements described or used herein are merely exemplary and not a limitation on the present invention. Other measurements can be used. Further, any specific materials noted herein are only examples: alternative implementations may employ differing materials.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An aircraft comprising:
a fuselage defining a cabin interior, and
an environmental control system that includes
a source of air, wherein air flows between the source of air and the cabin interior along an airflow path,
a mixer unit in airflow communication with the source of air and positioned downstream from the source of air in the airflow path,
at least a first air duct positioned in the airflow path between the mixer unit and the cabin interior, and
a first fragrance dispensing unit positioned between the air source and the cabin interior along the airflow path, wherein the first fragrance dispensing unit is configured to dispense at least a first fragrance into the airflow path.

2. The aircraft of claim 1 wherein the first fragrance dispensing unit includes a scent assembly that contains a first fragrance oil that comprises the first fragrance.

3. The aircraft of claim 2 wherein the first fragrance dispensing unit is configured to selectively dispense at least first and second fragrances into the airflow path.

4. The aircraft of claim 1 wherein the first fragrance dispensing unit is configured to dispense the first fragrance into the mixer unit.

5. The aircraft of claim 1 wherein the first fragrance dispensing unit includes a first fragrance cartridge therein that includes a scent assembly with the first fragrance therein, wherein the first fragrance cartridge includes a cover that is movable between a closed position and an open position, wherein the first fragrance is dispensed when the cover is in the open position.

6. The aircraft of claim 5 wherein the first fragrance dispensing unit includes a second fragrance cartridge therein that includes a scent assembly with a second fragrance therein, wherein the second fragrance cartridge includes a cover that is movable between a closed position and an open position, wherein the second fragrance is dispensed when the cover is in the open position.

7. The aircraft of claim 5 wherein the fragrance dispensing unit includes a first fragrance module that includes a rotatable portion that is in engagement with the first cartridge, and wherein rotational movement of the rotatable portion moves the cover of the first cartridge between the open and closed positions along a linear path.

8. The aircraft of claim 1 wherein the first fragrance dispensing unit is configured to selectively dispense at least first and second fragrances into the first duct, and wherein a second fragrance dispensing unit is configured to selectively dispense at least first and second fragrances into a second duct.

9. The aircraft of claim 8 wherein the first fragrance dispensing unit includes a first fragrance cartridge therein that includes a scent assembly with the first fragrance therein, wherein the first fragrance cartridge includes a cover that is movable between a closed position and an open position, wherein the first fragrance is dispensed when the cover is in the open position, wherein the first fragrance dispensing unit includes a second fragrance cartridge therein that includes a scent assembly with the second fragrance therein, wherein the second fragrance cartridge includes a cover that is movable between a closed position and an open position, wherein the second fragrance is dispensed when the cover is in the open position.

10. The aircraft of claim 1 wherein the fragrance dispensing unit is in electrical communication with an electrical control unit, wherein the first fragrance dispensing unit is configured to selectively dispense the first fragrance based on instructions from the electrical control unit.

11. The aircraft of claim 10 wherein the electrical control unit includes a human machine interface, and wherein the instructions can be provided via human input.

12. An aircraft comprising:
a fuselage defining a cabin interior that includes at least a first zone, and
a fragrance delivery system disposed in the cabin interior, wherein the fragrance delivery system includes
a first fragrance dispensing unit positioned in the first zone, wherein the first fragrance dispensing unit includes a first fragrance cartridge that includes a first scent and a second fragrance cartridge that includes a second scent,
a first electronic control unit positioned in the first zone and in communication with the first fragrance dispensing unit,
a second fragrance dispensing unit positioned in the first zone, wherein the second fragrance dispensing unit is in communication with the first electrical control unit, and
a human machine interface in communication with the first electronic control unit,
wherein the first fragrance dispensing unit is configured to selectively dispense either the first fragrance or the second fragrance.

13. The aircraft of claim 12 wherein the first fragrance dispensing unit includes a first fragrance cartridge therein, wherein the first fragrance cartridge includes a first near field communication portion that includes information related to the first fragrance cartridge, wherein the first near field communication portion is in communication with a receiver in the first fragrance dispensing unit, and wherein the information related to the first fragrance cartridge is communicated to the human machine interface.

* * * * *